US012097041B2

(12) United States Patent
Burns et al.

(10) Patent No.: US 12,097,041 B2
(45) Date of Patent: *Sep. 24, 2024

(54) METHODS OF TREATING DEEP AND EARLY-STAGE PRESSURE INDUCED TISSUE DAMAGE

(71) Applicant: BRUIN BIOMETRICS, LLC, Los Angeles, CA (US)

(72) Inventors: Martin F. Burns, Los Angeles, CA (US); Vignesh Mani Iyer, Torrance, CA (US)

(73) Assignee: BRUIN BIOMETRICS, LLC, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/295,093

(22) Filed: Apr. 3, 2023

(65) Prior Publication Data
US 2023/0240592 A1 Aug. 3, 2023

Related U.S. Application Data

(63) Continuation of application No. 17/591,139, filed on Feb. 2, 2022, now Pat. No. 11,642,075.

(60) Provisional application No. 63/304,066, filed on Jan. 28, 2022, provisional application No. 63/145,349, filed on Feb. 3, 2021.

(51) Int. Cl.
A61B 5/00 (2006.01)
(52) U.S. Cl.
CPC ............ A61B 5/447 (2013.01); A61B 5/443 (2013.01)

(58) Field of Classification Search
CPC ........ A61B 5/447; A61B 5/443; A61B 5/4875
See application file for complete search history.

(56) References Cited

U.S. PATENT DOCUMENTS

| 3,851,641 A | 12/1974 | Toole et al. |
| 4,295,009 A | 10/1981 | Weidler |
| 4,557,271 A | 12/1985 | Stoller et al. |
| 4,857,716 A | 8/1989 | Gombrich et al. |

(Continued)

FOREIGN PATENT DOCUMENTS

| AU | 2020103438 A4 | 1/2021 |
| CA | 2811609 | 11/2011 |

(Continued)

OTHER PUBLICATIONS

Alanen, "Measurement of Hydration in the Stratum Corneum with the MoistureMeter and Comparison with the Corneometer," *Skin Research and Technology*, 10:32-37 (2004).

(Continued)

*Primary Examiner* — Rene T Towa
(74) *Attorney, Agent, or Firm* — Arnold & Porter Kaye Scholer LLP

(57) ABSTRACT

The present disclosure provides methods for evaluating tissue damage and the use of spatial variation in Sub-Epidermal Moisture (SEM) values to determine damaged tissue for clinical intervention. The present disclosure provides methods of identifying deep and early-stage pressure-induced injuries or ulcers (PI/PU). The present disclosure provides algorithm for computing SEM delta values which inform clinical decision-making for developing intact skin PI/PUs including suspected deep tissue injury (sDTI) and Stage I PI/PUs.

24 Claims, 5 Drawing Sheets

(56) References Cited

U.S. PATENT DOCUMENTS

| | | |
|---|---|---|
| 4,860,753 A | 8/1989 | Amerena |
| 5,001,436 A | 3/1991 | Scot |
| 5,073,126 A | 12/1991 | Kikuchi et al. |
| 5,152,296 A | 10/1992 | Simons |
| 5,284,150 A | 2/1994 | Butterfield et al. |
| 5,292,341 A | 3/1994 | Snell |
| 5,367,789 A | 11/1994 | Lamont |
| 5,815,416 A | 9/1998 | Liebmann et al. |
| 5,904,581 A | 5/1999 | Pope et al. |
| 6,204,749 B1 | 3/2001 | Ishihara |
| 6,223,088 B1 | 4/2001 | Scharnberg et al. |
| 6,254,435 B1 | 7/2001 | Cheong et al. |
| 6,312,263 B1 | 11/2001 | Higuchi et al. |
| 6,330,479 B1 | 12/2001 | Stauffer |
| 6,368,284 B1 | 4/2002 | Bardy |
| 6,370,426 B1 | 4/2002 | Campbell et al. |
| 6,434,422 B1 | 8/2002 | Tomoda et al. |
| 6,577,700 B1 | 6/2003 | Fan et al. |
| 6,634,045 B1 | 10/2003 | DuDonis et al. |
| 6,738,798 B1 | 5/2004 | Ploetz et al. |
| 6,756,793 B2 | 6/2004 | Hirono et al. |
| 6,963,772 B2 | 11/2005 | Bloom et al. |
| 7,079,899 B2 | 7/2006 | Petrofsky |
| 7,291,023 B1 | 11/2007 | Still et al. |
| 7,315,767 B2 | 1/2008 | Caduff et al. |
| 7,402,135 B2 | 7/2008 | Leveque et al. |
| 7,783,344 B2 | 8/2010 | Lackey et al. |
| 8,011,041 B2 | 9/2011 | Hann |
| 8,060,315 B2 | 11/2011 | Brosette et al. |
| 8,355,925 B2 | 1/2013 | Rothman et al. |
| 8,390,583 B2 | 3/2013 | Forutanpour et al. |
| 8,494,617 B2 | 7/2013 | Baker, Jr. et al. |
| 8,648,707 B2 | 2/2014 | Franz et al. |
| 8,690,785 B2 | 4/2014 | Lading |
| 8,925,392 B2 | 1/2015 | Esposito et al. |
| 9,028,407 B1 | 5/2015 | Bennett-Guerrero |
| 9,095,305 B2 | 8/2015 | Engler et al. |
| 9,220,455 B2 | 12/2015 | Sarrafzadeh et al. |
| 9,271,676 B2 | 3/2016 | Alanen et al. |
| 9,398,879 B2 | 7/2016 | Sarrafzadeh et al. |
| 9,675,289 B2 | 6/2017 | Heaton |
| 9,763,596 B2 | 9/2017 | Tonar et al. |
| 9,949,683 B2 | 4/2018 | Afentakis |
| 9,980,673 B2 | 5/2018 | Sarrafzadeh et al. |
| 10,085,643 B2 | 10/2018 | Bandic et al. |
| 10,166,387 B2 | 1/2019 | Bergelin et al. |
| 10,178,961 B2 | 1/2019 | Tonar et al. |
| 10,182,740 B2 | 1/2019 | Tonar et al. |
| 10,188,340 B2 | 1/2019 | Sarrafzadeh et al. |
| 10,194,856 B2 | 2/2019 | Afentakis et al. |
| 10,206,604 B2 | 2/2019 | Bergelin et al. |
| 10,226,187 B2 | 3/2019 | Al-Ali et al. |
| 10,278,636 B2 | 5/2019 | Wu et al. |
| 10,285,898 B2 | 5/2019 | Douglas et al. |
| 10,307,060 B2 | 6/2019 | Tran |
| 10,342,482 B1 | 7/2019 | Lisy et al. |
| 10,383,527 B2 | 8/2019 | Al-Ali |
| 10,420,602 B2 | 9/2019 | Horton et al. |
| 10,441,185 B2 | 10/2019 | Rogers et al. |
| 10,448,844 B2 | 10/2019 | Al-Ali et al. |
| 10,463,293 B2 | 11/2019 | Maharbiz et al. |
| 10,485,447 B2 | 11/2019 | Tonar et al. |
| 10,898,129 B2 | 1/2021 | Burns et al. |
| 10,950,960 B2 | 3/2021 | Burns et al. |
| 10,959,664 B2 | 3/2021 | Burns et al. |
| 11,191,477 B2 | 12/2021 | Burns |
| 11,253,192 B2 | 2/2022 | Sarrafzadeh et al. |
| 11,284,810 B2 | 3/2022 | Tonar et al. |
| 11,304,652 B2 | 4/2022 | Burns et al. |
| 11,337,651 B2 | 5/2022 | Burns et al. |
| 11,342,696 B2 | 5/2022 | Burns et al. |
| 11,426,118 B2 | 8/2022 | Burns |
| 11,471,094 B2 | 10/2022 | Burns et al. |
| 11,534,077 B2 | 12/2022 | Tonar et al. |
| 11,600,939 B2 | 3/2023 | Burns et al. |
| 11,627,910 B2 | 4/2023 | Burns et al. |
| 11,642,075 B2 | 5/2023 | Burns et al. |
| 11,779,265 B2 | 10/2023 | Sarrafzadeh et al. |
| 11,824,291 B2 | 11/2023 | Burns et al. |
| 11,832,929 B2 | 12/2023 | Tonar et al. |
| 11,980,475 B2 | 5/2024 | Burns et al. |
| 2001/0049609 A1 | 12/2001 | Girouard et al. |
| 2001/0051783 A1 | 12/2001 | Edwards et al. |
| 2002/0016535 A1 | 2/2002 | Martin et al. |
| 2002/0032485 A1 | 3/2002 | Flam et al. |
| 2002/0070866 A1 | 6/2002 | Newham |
| 2002/0112898 A1 | 8/2002 | Honda et al. |
| 2002/0143262 A1 | 10/2002 | Bardy |
| 2003/0009244 A1 | 1/2003 | Engleson et al. |
| 2003/0036674 A1 | 2/2003 | Bouton |
| 2003/0036713 A1 | 2/2003 | Bouton et al. |
| 2003/0110662 A1 | 6/2003 | Gilman et al. |
| 2003/0116447 A1 | 6/2003 | Surridge et al. |
| 2003/0130427 A1 | 7/2003 | Cleary et al. |
| 2003/0139255 A1 | 7/2003 | Lina |
| 2003/0199783 A1 | 10/2003 | Bloom et al. |
| 2004/041029 A1 | 3/2004 | Postman et al. |
| 2004/0046668 A1 | 3/2004 | Smith et al. |
| 2004/0054298 A1 | 3/2004 | Masuo et al. |
| 2004/0080325 A1 | 4/2004 | Ogura |
| 2004/0133092 A1 | 7/2004 | Kain |
| 2004/0147977 A1 | 7/2004 | Petrofsky |
| 2004/0171962 A1 | 9/2004 | Leveque et al. |
| 2004/0176754 A1 | 9/2004 | Island et al. |
| 2004/0236200 A1 | 11/2004 | Say et al. |
| 2004/0254457 A1 | 12/2004 | Van Der Weide |
| 2005/0027175 A1 | 2/2005 | Yang |
| 2005/0070778 A1 | 3/2005 | Lackey et al. |
| 2005/0086072 A1 | 4/2005 | Fox, Jr. et al. |
| 2005/0096513 A1 | 5/2005 | Ozguz et al. |
| 2005/0177061 A1 | 8/2005 | Alanen et al. |
| 2005/0203435 A1 | 9/2005 | Nakada |
| 2005/0215918 A1 | 9/2005 | Frantz et al. |
| 2005/0245795 A1 | 11/2005 | Goode et al. |
| 2005/0251418 A1 | 11/2005 | Fox, Jr. et al. |
| 2006/0052678 A1 | 3/2006 | Drinan et al. |
| 2006/0058593 A1 | 3/2006 | Drinan et al. |
| 2006/0097949 A1 | 5/2006 | Luebke et al. |
| 2006/0206013 A1 | 9/2006 | Rothman et al. |
| 2006/0239547 A1 | 10/2006 | Robinson et al. |
| 2007/0043282 A1 | 2/2007 | Mannheimer et al. |
| 2007/0051362 A1 | 3/2007 | Sullivan et al. |
| 2007/0106172 A1 | 5/2007 | Abreu |
| 2007/0179585 A1 | 8/2007 | Chandler et al. |
| 2007/0185392 A1 | 8/2007 | Sherman et al. |
| 2007/0191273 A1 | 8/2007 | Ambati et al. |
| 2007/0213700 A1 | 9/2007 | Davison et al. |
| 2007/0248542 A1 | 10/2007 | Kane et al. |
| 2008/0009764 A1 | 1/2008 | Davies |
| 2008/0015894 A1 | 1/2008 | Miller et al. |
| 2008/0027509 A1 | 1/2008 | Andino et al. |
| 2008/0039700 A1 | 2/2008 | Drinan et al. |
| 2008/0048680 A1 | 2/2008 | Hargreaves et al. |
| 2008/0054276 A1 | 3/2008 | Vogel et al. |
| 2008/0063363 A1 | 3/2008 | Kientz et al. |
| 2008/0166268 A1 | 7/2008 | Yamaguchi et al. |
| 2008/0259577 A1 | 10/2008 | Hu et al. |
| 2008/0278336 A1 | 11/2008 | Ortega et al. |
| 2009/0047694 A1 | 2/2009 | Shuber |
| 2009/0054752 A1 | 2/2009 | Jonnalagadda et al. |
| 2009/0076410 A1 | 3/2009 | Libbus et al. |
| 2009/0104797 A1 | 4/2009 | Tseng et al. |
| 2009/0124924 A1 | 5/2009 | Eror et al. |
| 2009/0189092 A1 | 7/2009 | Aoi et al. |
| 2009/0209830 A1 | 8/2009 | Nagle et al. |
| 2009/0285785 A1 | 11/2009 | Jimi et al. |
| 2009/0306487 A1 | 12/2009 | Crowe et al. |
| 2009/0326346 A1 | 12/2009 | Kracker et al. |
| 2010/0017182 A1 | 1/2010 | Voros et al. |
| 2010/0030167 A1 | 2/2010 | Thirstrup et al. |
| 2010/0042389 A1 | 2/2010 | Farruggia et al. |
| 2010/0073170 A1 | 3/2010 | Siejko et al. |
| 2010/0113979 A1 | 5/2010 | Sarrafzadeh et al. |
| 2010/0152551 A1 | 6/2010 | Hsu et al. |

(56) References Cited

U.S. PATENT DOCUMENTS

| | | |
|---|---|---|
| 2010/0268111 A1 | 10/2010 | Drinan et al. |
| 2010/0298687 A1 | 11/2010 | Yoo et al. |
| 2010/0312233 A1 | 12/2010 | Furnish et al. |
| 2010/0324455 A1 | 12/2010 | Rangel et al. |
| 2010/0324611 A1 | 12/2010 | Deming et al. |
| 2011/0046505 A1 | 2/2011 | Cornish et al. |
| 2011/0160548 A1 | 6/2011 | Forster |
| 2011/0175844 A1 | 7/2011 | Berggren et al. |
| 2011/0184264 A1 | 7/2011 | Galasso, Jr. et al. |
| 2011/0191122 A1 | 8/2011 | Kharraz Tavakol et al. |
| 2011/0223078 A1 | 9/2011 | Ohashi |
| 2011/0237926 A1 | 9/2011 | Jensen |
| 2011/0263950 A1 | 10/2011 | Larson et al. |
| 2011/0301441 A1 | 12/2011 | Bandic et al. |
| 2011/0313311 A1 | 12/2011 | Gaw |
| 2012/0029410 A1 | 2/2012 | Koenig et al. |
| 2012/0061257 A1 | 3/2012 | Yu et al. |
| 2012/0078088 A1 | 3/2012 | Whitestone et al. |
| 2012/0150011 A1 | 6/2012 | Besio |
| 2012/0179006 A1 | 7/2012 | Jansen et al. |
| 2012/0190989 A1 | 7/2012 | Kaiser et al. |
| 2012/0271121 A1 | 10/2012 | Della Torre et al. |
| 2013/0041235 A1 | 2/2013 | Rogers et al. |
| 2013/0072870 A1 | 3/2013 | Heppe et al. |
| 2013/0121544 A1 | 5/2013 | Sarrafzadeh et al. |
| 2013/0123587 A1 | 5/2013 | Sarrafzadeh et al. |
| 2013/0137951 A1 | 5/2013 | Chuang et al. |
| 2013/0253285 A1 | 9/2013 | Bly et al. |
| 2013/0261496 A1 | 10/2013 | Engler et al. |
| 2013/0301255 A1 | 11/2013 | Kim et al. |
| 2013/0310440 A1 | 11/2013 | Duskin et al. |
| 2013/0333094 A1 | 12/2013 | Rogers et al. |
| 2013/0338661 A1 | 12/2013 | Behnke, II |
| 2014/0121479 A1 | 5/2014 | O'Connor et al. |
| 2014/0142984 A1 | 5/2014 | Wright et al. |
| 2014/0200486 A1 | 7/2014 | Bechtel et al. |
| 2014/0221792 A1 | 8/2014 | Miller et al. |
| 2014/0273025 A1 | 9/2014 | Hurskainen et al. |
| 2014/0275823 A1 | 9/2014 | Lane et al. |
| 2014/0288397 A1 | 9/2014 | Sarrafzadeh et al. |
| 2014/0298928 A1 | 10/2014 | Duesterhoft et al. |
| 2014/0316297 A1 | 10/2014 | McCaughan et al. |
| 2014/0318699 A1 | 10/2014 | Longinotti-Buitoni et al. |
| 2015/0002168 A1 | 1/2015 | Kao et al. |
| 2015/0009168 A1 | 1/2015 | Levesque et al. |
| 2015/0094548 A1 | 4/2015 | Sabatini et al. |
| 2015/0157435 A1 | 6/2015 | Chasins et al. |
| 2015/0186607 A1 | 7/2015 | Gileijnse et al. |
| 2015/0230863 A1 | 8/2015 | Youngquist et al. |
| 2015/0343173 A1 | 12/2015 | Tobescu et al. |
| 2015/0363567 A1 | 12/2015 | Pettus |
| 2015/0366499 A1 | 12/2015 | Sarrafzadeh et al. |
| 2015/0371522 A1 | 12/2015 | Mravyan et al. |
| 2016/0015962 A1 | 1/2016 | Shokoueinejad Maragheh et al. |
| 2016/0038055 A1 | 2/2016 | Wheeler et al. |
| 2016/0058342 A1 | 3/2016 | Maiz-Aguinaga et al. |
| 2016/0072308 A1 | 3/2016 | Nyberg et al. |
| 2016/0100790 A1 | 4/2016 | Cantu et al. |
| 2016/0101282 A1 | 4/2016 | Bergelin et al. |
| 2016/0166438 A1 | 6/2016 | Rovaniemi |
| 2016/0174631 A1 | 6/2016 | Tong et al. |
| 2016/0174871 A1 | 6/2016 | Sarrafzadeh et al. |
| 2016/0220172 A1 | 8/2016 | Sarrafzadeh et al. |
| 2016/0270672 A1 | 9/2016 | Chen et al. |
| 2016/0270968 A1 | 9/2016 | Stanford et al. |
| 2016/0278692 A1 | 9/2016 | Larson et al. |
| 2016/0296268 A1 | 10/2016 | Gee et al. |
| 2016/0310034 A1* | 10/2016 | Tonar .................. A61B 5/445 |
| 2016/0338591 A1 | 11/2016 | Lachenbruch et al. |
| 2017/0007153 A1 | 1/2017 | Tonar et al. |
| 2017/0014044 A1 | 1/2017 | Tonar et al. |
| 2017/0014045 A1 | 1/2017 | Tonar et al. |
| 2017/0105646 A1 | 4/2017 | Bryenton et al. |
| 2017/0156658 A1 | 6/2017 | Maharbiz et al. |
| 2017/0172489 A1 | 6/2017 | Afentakis |
| 2017/0188841 A1 | 7/2017 | Ma et al. |
| 2017/0238849 A1 | 8/2017 | Chapman et al. |
| 2017/0255812 A1 | 9/2017 | Kwon |
| 2017/0311807 A1 | 11/2017 | Fu et al. |
| 2017/0319073 A1 | 11/2017 | DiMaio et al. |
| 2018/0020058 A1 | 1/2018 | Martines et al. |
| 2018/0045725 A1 | 2/2018 | Yoo et al. |
| 2018/0220924 A1* | 8/2018 | Burns .................. A61B 5/0537 |
| 2018/0220953 A1 | 8/2018 | Burns et al. |
| 2018/0220954 A1 | 8/2018 | Burns et al. |
| 2018/0220961 A1 | 8/2018 | Burns et al. |
| 2018/0360344 A1 | 12/2018 | Burns et al. |
| 2019/0000352 A1 | 1/2019 | Everett et al. |
| 2019/0038133 A1 | 2/2019 | Tran |
| 2019/0053751 A1 | 2/2019 | Torres |
| 2019/0060602 A1 | 2/2019 | Tran et al. |
| 2019/0069836 A1 | 3/2019 | Hettrick |
| 2019/0104981 A1 | 4/2019 | Sarrafzadeh et al. |
| 2019/0104982 A1 | 4/2019 | Dunn et al. |
| 2019/0117964 A1 | 4/2019 | Bahrami et al. |
| 2019/0134396 A1 | 5/2019 | Toth et al. |
| 2019/0142333 A1 | 5/2019 | Burns et al. |
| 2019/0147990 A1 | 5/2019 | Burns et al. |
| 2019/0148901 A1 | 5/2019 | Komoto |
| 2019/0150882 A1 | 5/2019 | Maharbiz et al. |
| 2019/0175098 A1 | 6/2019 | Burns et al. |
| 2019/0192066 A1 | 6/2019 | Schoess et al. |
| 2019/0246972 A1 | 8/2019 | Burns et al. |
| 2019/0282436 A1 | 9/2019 | Douglas et al. |
| 2019/0290189 A1 | 9/2019 | Sarrafzadeh et al. |
| 2019/0307360 A1 | 10/2019 | Tonar et al. |
| 2019/0307405 A1 | 10/2019 | Terry et al. |
| 2020/0008299 A1 | 1/2020 | Tran et al. |
| 2020/0043607 A1 | 2/2020 | Zerhusen et al. |
| 2020/0069240 A1 | 3/2020 | Burns |
| 2020/0069241 A1 | 3/2020 | Burns |
| 2020/0069242 A1 | 3/2020 | Burns et al. |
| 2020/0077892 A1 | 3/2020 | Tran |
| 2020/0078499 A1 | 3/2020 | Gadde et al. |
| 2020/0093395 A1 | 3/2020 | Tonar et al. |
| 2020/0100723 A1 | 4/2020 | Burns |
| 2020/0113488 A1 | 4/2020 | Al-Ali et al. |
| 2020/0127398 A1 | 4/2020 | Burns et al. |
| 2020/0296821 A1 | 9/2020 | Trublowski et al. |
| 2020/0297244 A1 | 9/2020 | Brownhill et al. |
| 2020/0297255 A1 | 9/2020 | Martinez et al. |
| 2021/0307635 A1 | 10/2021 | Burns |
| 2022/0071555 A1 | 3/2022 | Burns et al. |
| 2022/0192587 A1 | 6/2022 | Burns et al. |
| 2022/0211291 A1 | 7/2022 | Tonar et al. |
| 2022/0240840 A1 | 8/2022 | Burns |
| 2022/0273238 A1 | 9/2022 | Burns et al. |
| 2022/0287584 A1 | 9/2022 | Burns et al. |
| 2022/0330847 A1 | 10/2022 | Burns et al. |
| 2022/0409086 A1 | 12/2022 | Burns |
| 2023/0109698 A1 | 4/2023 | Tonar et al. |
| 2023/0148893 A1 | 5/2023 | Burns et al. |
| 2023/0363698 A9 | 5/2023 | Burns |
| 2023/0337966 A1 | 6/2023 | Sarrafzadeh et al. |
| 2023/0329629 A1 | 10/2023 | Burns et al. |
| 2024/0039192 A1 | 2/2024 | Burns et al. |
| 2024/0081727 A1 | 3/2024 | Burns |
| 2024/0138696 A1 | 5/2024 | Burns et al. |

FOREIGN PATENT DOCUMENTS

| | | |
|---|---|---|
| CA | 2609842 C | 10/2016 |
| CN | 204119175 U | 1/2015 |
| CN | 104352230 A | 2/2015 |
| CN | 104567657 A | 4/2015 |
| CN | 105578333 A | 5/2016 |
| CN | 105963074 A | 9/2016 |
| CN | 208111467 U | 11/2018 |
| DE | 102012011212 A1 | 12/2012 |
| EP | 0970656 A1 | 1/2000 |
| EP | 1080687 A1 | 3/2001 |
| EP | 1372475 B1 | 1/2004 |
| EP | 1569553 A1 | 9/2005 |
| EP | 3092946 A1 | 11/2016 |

(56) References Cited

FOREIGN PATENT DOCUMENTS

| | | |
|---|---|---|
| EP | 3280488 B1 | 12/2018 |
| GB | 2584808 A | 12/2020 |
| JP | 2000-060805 A | 2/2000 |
| JP | 2001-178705 | 7/2001 |
| JP | 2001-326773 A | 11/2001 |
| JP | 2003-169787 A | 6/2003 |
| JP | 2003-169788 A | 6/2003 |
| JP | 2003-290166 A | 10/2003 |
| JP | 2005-52227 | 3/2005 |
| JP | 2009-268611 A | 11/2009 |
| JP | 4418419 | 2/2010 |
| JP | 2013-198639 A | 10/2013 |
| JP | 2015-134074 | 7/2015 |
| KR | 10-2014-0058445 | 5/2014 |
| WO | 1996/010951 A1 | 4/1996 |
| WO | 2001/054580 A1 | 8/2001 |
| WO | 2002/080770 A1 | 10/2002 |
| WO | 2004/105602 A1 | 12/2004 |
| WO | 2005/099644 A2 | 10/2005 |
| WO | 2006/029035 A1 | 3/2006 |
| WO | 2007/098762 A1 | 9/2007 |
| WO | 2009/144615 A1 | 12/2009 |
| WO | 2010/060102 A2 | 5/2010 |
| WO | 2011/004165 A1 | 1/2011 |
| WO | 2011/022418 A2 | 2/2011 |
| WO | 2011/048556 A2 | 4/2011 |
| WO | 2011/080080 A1 | 7/2011 |
| WO | 2011/080262 A1 | 7/2011 |
| WO | 2011/091517 A1 | 8/2011 |
| WO | 2011/143071 A2 | 11/2011 |
| WO | 2013/033724 A1 | 3/2013 |
| WO | 2013/114356 A1 | 8/2013 |
| WO | 2013/116242 A2 | 8/2013 |
| WO | 2013/140714 A1 | 9/2013 |
| WO | 2014/186894 A1 | 11/2014 |
| WO | 2015/003015 A2 | 1/2015 |
| WO | 2015/022583 A2 | 2/2015 |
| WO | 2015/077838 A1 | 6/2015 |
| WO | 2015/168720 A1 | 11/2015 |
| WO | 2015/169911 A1 | 11/2015 |
| WO | 2015/195720 A1 | 12/2015 |
| WO | 2016/098062 A1 | 6/2016 |
| WO | 2016/172263 A1 | 10/2016 |
| WO | 2016/172264 A1 | 10/2016 |
| WO | 2017/032393 | 3/2017 |
| WO | 2017/214188 A1 | 12/2017 |
| WO | 2017/218818 A2 | 12/2017 |
| WO | 2018/071715 A1 | 4/2018 |
| WO | 2018/077560 A1 | 5/2018 |
| WO | 2018/115461 A1 | 6/2018 |
| WO | 2018/144938 | 8/2018 |
| WO | 2018/144941 | 8/2018 |
| WO | 2018/144943 | 8/2018 |
| WO | 2018/144946 | 8/2018 |
| WO | 2018/168424 A1 | 9/2018 |
| WO | 2018/189265 A1 | 10/2018 |
| WO | 2018/209100 A1 | 11/2018 |
| WO | 2018/234443 A1 | 12/2018 |
| WO | 2018/236739 | 12/2018 |
| WO | 2019/020551 A1 | 1/2019 |
| WO | 2019/030384 A2 | 2/2019 |
| WO | 2019/048624 A1 | 3/2019 |
| WO | 2019/048626 A1 | 3/2019 |
| WO | 2019/048638 A1 | 3/2019 |
| WO | 2019/072531 A1 | 4/2019 |
| WO | 2019/073389 A1 | 4/2019 |
| WO | 2019/076967 A2 | 4/2019 |
| WO | 2019/096828 A1 | 5/2019 |
| WO | 2019/099810 A1 | 5/2019 |
| WO | 2019/099812 A1 | 5/2019 |
| WO | 2019/113481 | 6/2019 |
| WO | 2019/157290 | 8/2019 |
| WO | 2019/162272 A1 | 8/2019 |
| WO | 2020/014779 A1 | 1/2020 |
| WO | 2020/043806 A1 | 3/2020 |
| WO | 2020/053290 A1 | 3/2020 |
| WO | 2020/077100 A1 | 4/2020 |
| WO | 2020/187643 A1 | 9/2020 |
| WO | 2020/187851 A1 | 9/2020 |
| WO | 2020/234429 A2 | 11/2020 |

OTHER PUBLICATIONS

Alberts et al., "The Extracellular Matrix of Animals," Molecular Biology of the Cell, 4th ed., pp. 1065-1127 (2002).

Allman et al., "Pressure Ulcer Risk Factors Among Hospitalized Patients with Activity Limitation," *JAMA*, 273:865-870 (1995).

Anonymous, "Recommended Practices for Positioning the Patient in the Perioperative Practice Setting," in *Perioperative Standards, Recommended Practices, and Guidelines*, AORN, Inc., 525-548 (2006).

Arao et al., "Morphological Characteristics of the Dermal Papillae in the Development of Pressure Sores," *World Wide Wounds* (Mar. 1999), 6 pages (obtained online).

Australian Intellectual Property Office, Office Action issued on May 1, 2014, for corresponding Australian patent application No. 2011253253 (pp. 1-10) and pending claims (pp. 11-15) pp. 1-15.

Australian Patent Office, Office Action issued on Jun. 1, 2015, for corresponding Australian Patent Application No. 2011253253 (pp. 1-4) and claims (pp. 5-10) pp. 1-10.

Bader et al., "Effect of Externally Applied Skin Surface Forces on Tissue Vasculature," *Archives of Physical Medicine and Rehabilitation*, 67(11):807-11(1986).

Barnes, "Moisture Meters for Use on Thin Lumber and Veneers," *Moisture Register Co.*, 1-5 (1956).

Bates-Jensen et al., "Subepidermal Moisture Predicts Erythema and Stage 1 Pressure Ulcres in Nursing Home Residents: A Pilot Study," Journal of the American Geriatric Society, 55:1199-1205 (2007).

Bates-Jensen et al., "Subepidermal moisture differentiates erythema and stage 1 pressure ulcers in nursing home residents," Wound Repair Regeneration, 16:189-197 (2008).

Bates-Jensen et al., "Subepidermal Moisture is Associated with Early Pressure Ulcer Damage in Nursing Home Residents with Dark Skin Tones; Pilot Findings," Journal of Wound Ostomy and Continence Nursing, 36(3):277-284 (2009).

Bates-Jensen et al., "Subepidermal Moisture Detection of Pressure Induces Tissue Damage on the Trunk: The Pressure Ulcer Detection Study Outcomes," Wound Repair and Regeneration, 25:502-511 (2017).

Berggren, "Capacitive Biosensors," Electroanalysis, 13(3):173-180 (2001), Wiley-VCH (publisher), Weinheim, Germany.

Bergstrand et al., "Pressure-induced Vasodilation and Reactive Hyperemia at Different Depths in Sacral Tissue Under Clinically Relevant Conditions," Microcirculation, 21:761-771 (2014).

Bergstrom et al., "Pressure Ulcers in Adults: Prediction and Prevention," Clinical Practice Guideline—Quick Reference Guide for Clinicians, 117 (1992).

Black et al., "Differential Diagnosis of Suspected Deep Tissue Injury," *International Wound Journal*, 13(4):531-539 (2015).

Brem et al., "Protocol for the Successful Treatment of Pressure Ulcers," *The American Journal of Surgery*, 188 (Suppl. To Jul. 2004):9S-17S (2004).

Brem et al., "High cost of stage IV pressure ulcers," American Journal of Surgery, 200:473-477 (2010).

Brienza et al., "Friction-Induced Skin Injuries—Are They Pressure Ulcers?," Journal of Wound Ostomy and Continence Nursing, 42(1):62-64 (2015).

Carmo-Araujo et al., "Ischaemia and reperfusion effects on skeletal muscle tissue: morphological and histochemical studies," International Journal of Experimental Pathology, 88:147-154 (2007).

Ceelen et al., "Compression-induced damage and internal tissue strains are related," Journal of Biomechanics, 41:3399-3404 (2008).

Ching et al., "Tissue electrical properties monitoring for the prevention of pressure sore," Prosthetics and Orthotics International, 35(4):386-394 (2011).

(56) References Cited

OTHER PUBLICATIONS

Clendenin et al., "Inter-operator and inter-device agreement and reliability of the SEM Scanner," Journal of Tissue Viability, 24(1):17-23 (2015).
De Lorenzo et al., "Predicting body cell mass with bioimpedance by using theoretical methods: a technological review," Journal of Applied Physiology, 82(5):1542-1558 (1997).
de Oliveira et al., "Sub-epidermal moisture versus tradition and visual skin assessments to assess pressure ulcer risk in surgery patients," Journal of Wound Care, 31(3):254-264 (2022), Mark Allen Group (pub.) (obtained online).
Demarre et al., "The cost of pressure ulcer prevention and treatment in hospitals and nursing homes in Flanders: A cost-of-illness study," International Journal of Nursing Studies, 1-14 (2015).
Dodde et al., "Bioimpedance of soft tissue under compression," Physiology Measurement, 33(6):1095-1109 (2012).
Dupont, "Pyralux® FR Coverlay, Bondply & Sheet Adhesive," webpage, Retrieved from: www2.dupont.com/Pyralux/en_US/products/adhesives_films/FR/FR_films_html pp. 1-2 (2012).
DuPont, "General Specifications for Kapton Polyimide Film," Retrieved from Dupont: http://www2.dupont.com/Kapton/en_US/assets/downloads/pdf/Gen_Specs.pdf, pp. 1-7 (2012).
DuPont, "Pyralux® FR Copper-clad Laminate," webpage, Retrieved from: www2.dupont.com/Pymluxlen_US/productsllaminate/FR/pyralux_fr.html, pp. 1-2 (2012).
Eberlein-Gonska et al., "The Incidence and Determinants of Decubitus Ulcers in Hospital Care: An Analysis of Routine Quality Management Data at a University Hospital," Deutsches Arzteblatt International, 110(33-34):550-556 (2013).
European Patent Office, ESSR issued on Aug. 22, 2014, for corresponding European Patent Application No. 11781061.4 (pp. 1-7) and pending claims (pp. 3-10) pp. 1-10.
European Patent Office, Office Action issued on Jul. 13, 2015, for corresponding European Patent Application No. 11781061.4 (pp. 1-5) and claims (pp. 6-9) pp. 1-9.
Extended European Search Report mailed Aug. 30, 2016, in European Patent Application No. 16169670.
Extended European Search Report mailed Oct. 18, 2016, in European Patent Application No. 16166483.4.
Extended European Search Report dated Mar. 13, 2017, in European Patent Application No. 16196899.5.
Extended European Search Report mailed Oct. 25, 2019, in European Patent Application No. 19186393.5.
Extended European Search Report mailed Nov. 19, 2019, in European Patent Application No. 19190000.0.
Extended European Search Report mailed Feb. 6, 2020, in European Patent Application No. 18748733.5.
Extended European Search Report mailed Feb. 10, 2020, in European Patent Application No. 18748025.6.
Extended European Search Report mailed Feb. 10, 2020, in European Patent Application No. 18748512.3.
Extended European Search Report mailed Jun. 24, 2020, in European Patent Application No. 18747707.0.
Extended European Search Report dated Mar. 17, 2022, in European Patent Application No. 19838240.0.
Extended European Search Report dated May 24, 2022, in European Patent Application No. 19871332.3.
Extended European Search Report dated Feb. 1 2023, in European Patent Application No. 22211200.
Ford, "Hospice Wins Award for Innovation in Pressure Ulcer Prevention," *Nursing Times*, downloaded and printed on Apr. 18, 2020, from https://www.nursingtimes.net/news/research-and-innovation/hospice-wins-award-for-innovation-in-pressure-ulcer-prevention-30-11-2018/ (2018).
Gabriel et al., "The dielectric properties of biological tissues: II. Measurements in the frequency range 10 Hz to 20 GHz," Physics in Medicine and Biology, 41:2251-69 (1996).
Gabriel, "Compilation of the Dielectric Properties of Body Tissues at Rf and Microwave Frequencies Report," Occupational and Environmental Health Directorate, (1996).
Gardiner et al., "Incidence of hospital-acquired pressure ulcers—a population-based cohort study," International Wound Journal, 11(6):697-700 (2014).
Gershon et al., "SEM Scanner Readings to Assess Pressure Induced Tissue Damage," Proceedings of the 17th Annual European Pressure Ulcer Advisory Panel (EPUAP) meeting, Stockholm, Sweden (2014).
Gonzalez-Correa et al., "Electrical bioimpedance readings increase with higher pressure applied to the measuring probe," Physiology Measurement, 26:S39-S47 (2005).
Great Britain Search Report dated Apr. 27, 2020, in Great Britain Patent Application No. GB2002889.0.
Great Britain Search Report dated Jun. 28, 2021, in Great Britain Patent Application No. GB2106848.1.
Great Britain Search Report dated Feb. 9, 2022, in Great Britain Patent Application No. GB2118088.0.
Great Britain Search Report dated Feb. 14, 2022, in Great Britain Patent Application No. GB2118092.2.
Guihan et al., "Assessing the feasibility of subepidermal moisture to predict erythema and stage 1 pressure ulcers in persons with spinal cord injury: A pilot study," Journal of Spinal Cord Medicine, 35(1):46-52 (2012).
Hamazoto et al., "Estimate of Burn Depth by Non-Invasive Capacitance Measurement," *Japan Soc. ME & BE*, 42:266 (Jun. 2003).
Harrow, "Subepidermal moisture surrounding pressure ulcers in persons with a spinal cord injury: A pilot study," Journal of Spinal Cord Medicine, 37(6):719-728 (2014).
Hou, "Section IV. Osteofascial Compartment Syndrome," Limbs Trauma, 7:215-217 (2016), Hubei Science & Technology Publishing House (pub.), Wuhan, China.
Houwing et al., "Pressure-induced skin lesions in pigs: reperfusion injury and the effects of vitamin E," Journal of Wound Care, 9(1):36-40 (2000).
Huang et al., "A device for skin moisture and environment humidity detection," Sensors and Actuators B: Chemical, 206-212 (2008).
International Search Report and Written Opinion mailed Feb. 9, 2012, for International Patent Application No. PCT/US2011/035618.
International Search Report and Written Opinion mailed Jul. 22, 2016, for International Patent Application No. PCT/US2016/28515.
International Search Report and Written Opinion mailed Jul. 26, 2016, for International Patent Application No. PCT/US2016/28516.
International Search Report mailed Apr. 12, 2018, issued in International Patent Application No. PCT/US2018/016731.
International Search Report mailed Apr. 12, 2018, issued in International Patent Application No. PCT/US2018/016738.
International Search Report mailed Apr. 26, 2018, issued in International Patent Application No. PCT/US2018/016741.
International Search Report mailed Jul. 12, 2018, issued in International Patent Application No. PCT/US2018/016736.
International Search Report mailed Sep. 10, 2018, issued in International Patent Application No. PCT/US2018/038055.
International Search Report mailed Jan. 29, 2019, issued in International Patent Application No. PCT/US2018/061494.
International Search Report mailed Feb. 5, 2019, issued in International Patent Application No. PCT/US2018/064527.
International Search Report mailed Feb. 11, 2019, issued in International Patent Application No. PCT/US2018/061497.
International Search Report mailed May 29, 2019, issued in International Patent Application No. PCT/US2019/017226.
International Search Report mailed Mar. 9, 2020, issued in International Patent Application No. PCT/US2019/055655.
International Search Report mailed Dec. 8, 2020, issued in International Patent Application PCT/US2020/051134.
International Search Report mailed Aug. 17, 2021, issued in International Patent Application PCT/US2021/023818.
International Search Report mailed May 13, 2022, issued in International Patent Application PCT/US2022/014913.
International Search Report mailed Aug. 2, 2022, issued in International Patent Application PCT/US2022/025508.
International Search Report mailed Aug. 15, 2022, issued in International Patent Application PCT/US2022/019338.

(56) References Cited

OTHER PUBLICATIONS

Jan et al., "Local cooling reduces skin ischemia under surface pressure in rats: an assessment by wavelet analysis of laser Doppler blood flow oscillations," Physiology Measurement, 33(10):1733-1745 (2012).
Jaskowski, "Evaluation of the Healing Process of Skin Wounds by Means of Skin Absolute Value of Electrical Impedance," Dermatol. Mon.schr., 172(4):223-228 (1986).
Jiang et al., "Ischemia-Repeffusion Injury-Induced Histological Changes Affecting Early Stage Pressure Ulcer Development in a Rat model," Ostomy Wound Management, 57:55-60 (2011).
Jiang et al., "Expression of cytokines, growth factors and apoptosis-related signal molecules in chronic pressure ulcer wounds healing," Spinal Cord, 52(2):145-151 (2014).
Jiricka et al., "Pressure Ulcer Risk factors in an ICU Population," American Journal of Critical Care, 4:361-367 (1995).
Kanai et al., "Electrical measurement of fluid distribution in legs and arms," Medical Progress through Technology Journal, 12:159-170 (1987).
Kasuya et al., "Potential application of in vivo imaging of impaired lymphatic duct to evaluate the severity of pressure ulcer in mouse model," Scientific Reports, 4:4173 (7 pages) (2014).
Lee, "CapSense Best Practices," Application Note 2394, 1-10 (2007).
Liu et al., "A Systematic Review of Electrical Stimulation for Pressure Ulcer Prevention and Treatment in People with Spinal Cord Injuries," The Journal of Spinal Cord Medicine, 37(6):703-718 (2014).
Loerakker et al., "Temporal Effects of Mechanical Loading on Deformation-Induced Damage in Skeletal Muscle Tissue," Annual Review of Biomedical Engineering, 38(8):2577-2587 (2010).
Loerakker et al., "The effects of deformation, ischemia, and reperfusion on the development of muscle damage during prolonged loading," Journal of Applied Physiology, 111(4):1168-1177 (2011).
Lyder et al., "Quality of Care for Hospitalized Medicare Patients at Risk for Pressure Ulcers," Archives of Internal Medicine,161:1549-1554 (2001).
Martinsen, "Bioimpedance and Bioelectricity Basics," Elsevier Academic Press, Chapters 1 and 10 (2015).
Mathiesen et al., "Are labour-intensive efforts to prevent pressure ulcers cost-effective?" Journal of Medical Economics, 16(10):1238-1245 (2013).
Matthie et al., "Analytic assessment of the various bioimpedance methods used to estimate body water," Journal of Applied Physiology, 84(5):1801-1816 (1998).
Miller et al., "Lymphatic Clearance during Compressive Loading," Lymphology, 14(4):161-166 (1981).
Moore et al., "A randomised controlled clinical trial of repositioning, using the 30° tilt, for the prevention of pressure ulcers," Journal of Clinical Nursing, 20:2633-2644 (2011).
Moore et al., "Pressure ulcer prevalence and prevention practices in care of the older person in the Republic of Ireland," Journal of Clinical Nursing, 21:362-371 (2012).
Moore et al., "A review of PU prevalence and incidence across Scandinavia, Iceland and Ireland (Part I)", Journal of Wound Care, 22(7):361-362, 364-368 (2013).
Moore et al., "Subepidermal Moisture (SEM) and Bioimpedance: A Literature Review of a Novel Method for Early Detection of Pressure-Induced Tissue Damage (Pressure Ulcers)," International Wound Journal, 14(2):331-337 (2016).
Moore, "Using SEM (Sub Epidermal Moisture) Measurement for Early Pressure Ulcer Detection," Institute for Pressure Injury Prevention, WCICT 2017 (Jun. 20-21), Manchester, UK, 7 pp., available at www.pressureinjuryprevention.com/wp-content/uploads/2017/07/ipip_Moore_Sub_Epidermal_Moisture_notes.pdf (2017) (obtained online).
Moore et al., "SEM Scanner Made Easy," Wounds International, pp. 1-6, available at www.woundsinternational.com (2018).

Mulasi, "Bioimpedance at the Bedside: Current Applications, Limitations, and Opportunities," Nutritional Clinical Practice, 30(2):180-193 (2015).
Musa et al., "Clinical impact of a sub-epidermal moisture scanner: what is the real-world use?," J. Wound Care, 30(3):2-11 (2021), Mark Allen Group (pub.) (obtained online).
National Pressure Ulcer Advisory Panel et al., "Prevention and Treatment of Pressure Ulcers: Clinical Practice Guideline," Cambridge Media, (2014).
Nixon et al., "Pathology, diagnosis, and classification of pressure ulcers: comparing clinical and imaging techniques," Wound Repair and Regeneration, 13(4):365-372 (2005).
Nuutinen et al., "Validation of a new dielectric device to assess changes of tissue water in skin and subcutaneous fat," Physiological Measurement, 25:447-454 (2004).
O'Goshi, "Skin conductance; validation of Skicon-200EX compared to the original model, Skicon-100," Skin Research and Technology, 13:13-18 (2007).
Oliveira, "The Accuracy of Ultrasound, Thermography, Photography and Sub-Epidermal Moisture as a Predictor of Pressure Ulcer Presence—a Systematic Review," RCSI, School of Nursing thesis (2015).
Oomens et al., "Pressure Induced Deep Tissue Injury Explained," Annual Review of Biomedical Engineering, 43(2):297-305 (2015).
Pang et al. (eds.) Diagnosis and Treatment of Diabetes, China Press of Traditional Chinese Medicine (publisher), Beijing, China, pp. 466-468 (Oct. 2016), with English Translation.
Rotaru et al., "Friction between Human Skin and Medical Textiles for Decubitus Prevention," Tribology International, 65:91-96 (2013).
Saxena, The Pocket Doctor: Obstetrics & Gynecology, pp. 76-77 (2017), Tianjin Science & Technology Translation & Publishing Co. Ltd. (pub.), Tianjin, China.
Scallan et al., "Chapter 4: Pathophysiology of Edema Formation," Capillary Fluid Exchange: Regulation, Functions, and Pathology, 47-61 (2010).
Schultz et al., "Extracellular matrix: review of its role in acute and chronic wounds," World Wide Wounds, 1-20 (2005).
Schwan, "Electrical properties of tissues and cells," Advances in Biology and Medical Physics, 15:148-199 (1957).
Seibert et al., "Technical Expert Panel Summary Report: Refinement of a Cross-Setting Pressure Ulcer/Injury Quality Measure for Skilled Nursing Facilities, Inpatient Rehabilitation Facilities, Long-Term Care Hospitals, and Home Health Agencies," RTI International Abt Associates, CMS Contract No. HHSM-500-2013-130151 49 pp. (Aug. 2019).
Sener et al., "Pressure ulcer-induced oxidative organ injury is ameliorated by beta-glucan treatment in rats," International Immunopharmacology, 6(5):724-732 (2006).
Sewchuck et al., "Prevention and Early Detection of Pressure Ulcers in Patients Undergoing Cardiac Surgery," AORN Journal, 84(1):75-96 (2006).
Sprigle et al., "Analysis of Localized Erythema Using Clinical Indicators and Spectroscopy," Ostomy Wound Management, 49:42-52 (2003).
Stekelenburg et al., "Role of ischemia and deformation in the onset of compression-induced deep tissue injury: MRI-based studies in a rat model," Journal of Applied Physiology, 102:2002-2011 (2007).
Stekelenburg et al., "Deep Tissue Injury: How Deep is Our Understanding?" Archives of Physical Medicine Rehabilitation, 89(7):1410-1413 (2008).
Supplementary Partial European Search Report dated Jan. 27, 2020, in European Patent Application No. 18747707.
Supplementary European Search Report dated Jul. 13, 2021, in European Patent Application No. 18887039.
Supplementary European Search Report dated Oct. 1, 2021, in European Patent Application No. 19751130.
Swisher et al., "Impedance sensing device enables early detection of pressure ulcers in vivo," Nature Communications, 6:6575-6584 (2015).
Thomas et al., "Hospital-Acquired Pressure Ulcers and Risk of Death," Journal of the American Geriatrics Society, 44:1435-1440 (1996).

(56) References Cited

OTHER PUBLICATIONS

Thomas, "Prevention and Treatment of Pressure Ulcers," *J. Am. Med. Dir. Assoc.*, 7:46-59 (2006).

Truong et al., "Pressure Ulcer Prevention in the Hospital Setting Using Silicone Foam Dressings," *Cureus*, 8(8):e730, pp. 1-6 (2016).

Tur et al., "Topical Hydrogen Peroxide Treatment of Ischemic Ulcers in the Guinea Pig: Blood Recruitment in Multiple Skin Sites," *J. Am. Acad. Dermatol.*, 33:217-221 (1995).

Valentinuzzi et al., "Bioelectrical Impedance Techniques in Medicine. Part II: Monitoring of Physiological Events by Impedance," Critical Reviews in Biomedical Engineering, 24(4-6):353-466 (1996).

Vangilder et al., "Results of Nine International Pressure Ulcer Prevalence Surveys: 1989 to 2005," Ostomy Wound Management, 54(2):40-54 (2008).

Vowden et al., "Diabetic Foot Ulcer or Pressure Ulcer? That Is the Question," *The Diabetic Foot Journal*, 18:62-66 (2015).

Wagner et al., "Bioelectrical Impedance as a Discriminator of Pressure Ulcer Risk," Advances in Wound care, 9(2):30-37 (1996).

Wang et al., "A Wireless Biomedical Instrument for Evidence-Based Tissue Wound Characterization," *Wireless Health*, pp. 222-223 (2010).

Wang, "Biomedical System for Monitoring Pressure Ulcer Development," UCLA Electronic Theses and Dissertations, California, USA, pp. 1-123 (2013).

Watanabe et al., "CT analysis of the use of the electrical impedance technique to estimate local oedema in the extremities in patients with lymphatic obstruction," Medical and Biological Engineering and Computing, 36(1):60-65 (1998).

Weiss, "Tissue destruction by neutrophils," The New England Journal of Medicine, 320(6):365-76 (1989).

Yang, *Handbook of Practical Burn Surgery*, p. 48 (2008), People's Military Medical Press (pub.), Beijing, China.

Zanibbi, "Pattern Recognition: An Overview," downloaded from https://www.cs.rit.edu/~rlaz/prec20092/slides/Overview.pdf, 30 pp. (2010).

Arimoto et al, "Non-Contact Skin Moisture Measurement Based on Near-Infrared Spectroscopy," *Applied Spectroscopy*, 58(12):1439-1446 (2004).

Avci et al, "Low-Level Laser (Light) Therapy (LLLT) in Skin: Stimulating, Healing, Restoring," *Seminars in Cutaneous Medicine and Surgery*, 32(1)41-52 (Mar. 2013).

Extended European Search Report completed Nov. 7, 2023, in European Patent Application No. 23188775.3.

Partial European Search Report dated Sep. 6, 2023, in European Application No. 23188775.3.

Ross et al., "Assessment of Sub-Epidermal Moisture by Direct Measurement of Tissue Biocapacitance," *Medical Engineering & Physics*, 73:92-99 (Jul. 26, 2019).

Supplementary Partial European Search Report completed Jan. 10, 2024, in European Patent Application No. 21782145.

Brunetti et al., "Validation of a sub-epidermal moisture scanner for early detection of pressure ulcers in an ex vivo porcine model of localized oedema," *J. Tissue Viability*, 32(4):508-515 (Jul. 8, 2023).

Chan et al., "Using Wireless Measuring Devices and Tablet PC to Improve the Efficiency of Vital Signs Data Collection in Hospital," 4 pp., 2014 IEEE International Symposium on Bioelectronics and Bioinformatics (IEEE ISBB 2014).

International Search Report mailed May 29, 2024, issued in International Patent Application No. PCT/US2023/074190.

Partial European Search Report completed Mar. 27, 2024, in European Patent Application No. 23208591.0.

Partial European Search Report completed Apr. 16, 2024, in European Patent Application No. 24151800.0.

Supplementary European Search Report completed May 8, 2024, in European Patent Application No. 21782145.

Visscher et al., "Face Masks for Noninvasive Ventilation: Fit, Excess Skin Hydration, and Pressure Ulcers," *Respiratory Care*, 60(11):1536-1547 (Nov. 2015).

Weber et al., "Remote Wound Monitoring of Chronic Ulcers," IEEE Transactions on Information Technology in Biomedicine, IEEE Service Center, Los Alamitos, CA, vol. 13(2):371-377 (Mar. 1, 2010).

\* cited by examiner

METHODS OF TREATING DEEP AND EARLY-STAGE PRESSURE INDUCED TISSUE DAMAGE

CROSS-REFERENCE TO RELATED APPLICATIONS

This application is a continuation of U.S. application Ser. No. 17/591,139 filed Feb. 2, 2022, now U.S. Pat. No. 11,642,075, which claims the benefit of priority of U.S. Provisional Application No. 63/145,349 filed Feb. 3, 2021, and U.S. Provisional Application No. 63/304,066 filed Jan. 28, 2022, each of which is herein incorporated by reference in its entirety.

BACKGROUND OF THE INVENTION

Field of the Invention

The present disclosure provides a method for evaluating the use of spatial variation in Sub-Epidermal Moisture (SEM) values to determine damaged tissue for clinical intervention.

Description of Related Art

Pressure injuries or ulcers (PI/PUs) remain a frequently reported preventable patient harm in many countries. Despite improving care pathways in PI/PU prevention, PI/PUs are the only hospital-acquired condition whose incidence has worsened since 2014. Annually, PI/PUs occur in more than 2.5 million US patients, and are linked to approximately 60,000 deaths. Management of PI/PUs is cost intensive: overall annual costs in the US are estimated to exceed $26.8 billion, with per-patient costs ranging from $500 to $70,000. In the UK, treating PI/PUs costs the NHS £0.5-2.1 billion annually, accounting for approximately 4% of total expenditure. The advent of COVID-19 has increased the number of patients requiring intensive care and the increased lengths of stay associated with COVID-19 treatment intensify the risk factors associated with PI/PUs and are likely to increase global incidence rates of PI/PUs.

Current standard of care (SoC) relies heavily on validated risk assessment tool scores (RATS) (e.g., Braden and Waterlow1) to evaluate a patient's risk of developing PI/PUs. RATs are supplemented by a skin and tissue assessment. (STA), using visual and palpation tests. Healthcare practitioners (HCPs) are guided to assess for changes in skin color, blanchability, temperature, hardness and other visible or palpable indicators of injury. Stage I PI/PUs are described as an area of 'persistent focal edema' in the International Classification for Disease (ICD-10 code L89).

Subjective clinical judgment of HCPs, informed by RATS and STAB have a sensitivity of 50.6% and specificity of 60.1%—in other words approaching randomness. Additionally, there is a diagnostic latency—a gap between the onset of microscopic damage and the time at which it is detected and confirmed at the skin surface under the current SoC. Early microscopic tissue damage and the associated inflammatory response results in fluctuations in localized tissue oedema, termed sub-epidermal moisture (SEM), a systemic response that unfolds even before visual epidermal skin damage. Current RATs and clinical judgement are ineffective in achieving timely detection of non-visible sub-epidermal injuries. This ineffectiveness is further exacerbated in darkly pigmented skin, Relying solely on current RATs and STAB, early detection of developing PI/PUs and timely, appropriate, anatomy-specific interventions is impossible without an objective diagnostic test.

SUMMARY OF THE INVENTION

In an aspect, the present disclosure provides for, and includes, methods for assessing tissue health at and around a target region, comprising the steps of: obtaining a first plurality of SEM measurements at a first plurality of locations within a first tissue assessment area, obtaining a second plurality of SEM measurements at a second plurality of locations within a second tissue assessment area, calculating a first average of the first plurality of SEM measurements, calculating a second average of the second plurality of SEM measurements, calculating a difference between the second average and the first average, flagging that the tissue is damaged if the difference is greater than or equal to a cut-off threshold.

In an aspect, a cut-off threshold is a predetermined number. In an aspect, a cut-off threshold is a number ranging from about 0.6 to about 0.9. In an aspect, a cut-off threshold is about 0.6. In an aspect, a cut-off threshold is about 0.7. In an aspect, a cut-off threshold is about 0.8. In an aspect, a cut-off threshold is about 0.9.

In an aspect, a first tissue assessment area is a circle centered on a target region and having a first radial distance. In an aspect, a second tissue assessment area is an annulus centered on a target region and having a second inner radial distance and a third outer radial distance from the target region. In an aspect, a second inner radial distance is greater than or equal to a first radial distance. In an aspect, a third outer radial distance is greater than a second inner radial distance.

In an aspect, a first plurality of locations comprises a location in the center of a circle. In an aspect, a first plurality of locations comprises spatially distinct points within a circle. In an aspect, a first plurality of locations comprises spatially distinct points along one or more concentric rings within a circle, and wherein the one or more concentric rings are centered on a target region. In an aspect, a first plurality of locations comprises spatially distinct points along two lines dividing a circle into four quadrants. In an aspect, a second plurality of locations comprises spatially distinct points within an annulus. In an aspect, a second plurality of locations comprises spatially distinct points along one or more concentric rings within an annulus, and wherein the one or more concentric rings are centered on a target region. In an aspect, a second plurality of locations comprises spatially distinct points along two lines dividing an annulus into four quadrants.

In an aspect, a first plurality of SEM measurements consists of 1 to 9 measurements. In an aspect, a second plurality of SEM measurements consists of 3 to 8 measurements. In an aspect, a target region is a bony prominence selected from the group consisting of a sacrum, a heel, a sternum, a scapula, an elbow, a thoracic spine, a trochanter, an ischium, and an ear. In an aspect, a target region is a flesh tissue. In an aspect, a target region is within an erythema. In an aspect, a target region is within a healthy tissue.

BRIEF DESCRIPTION OF THE FIGURES

Some aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1A:
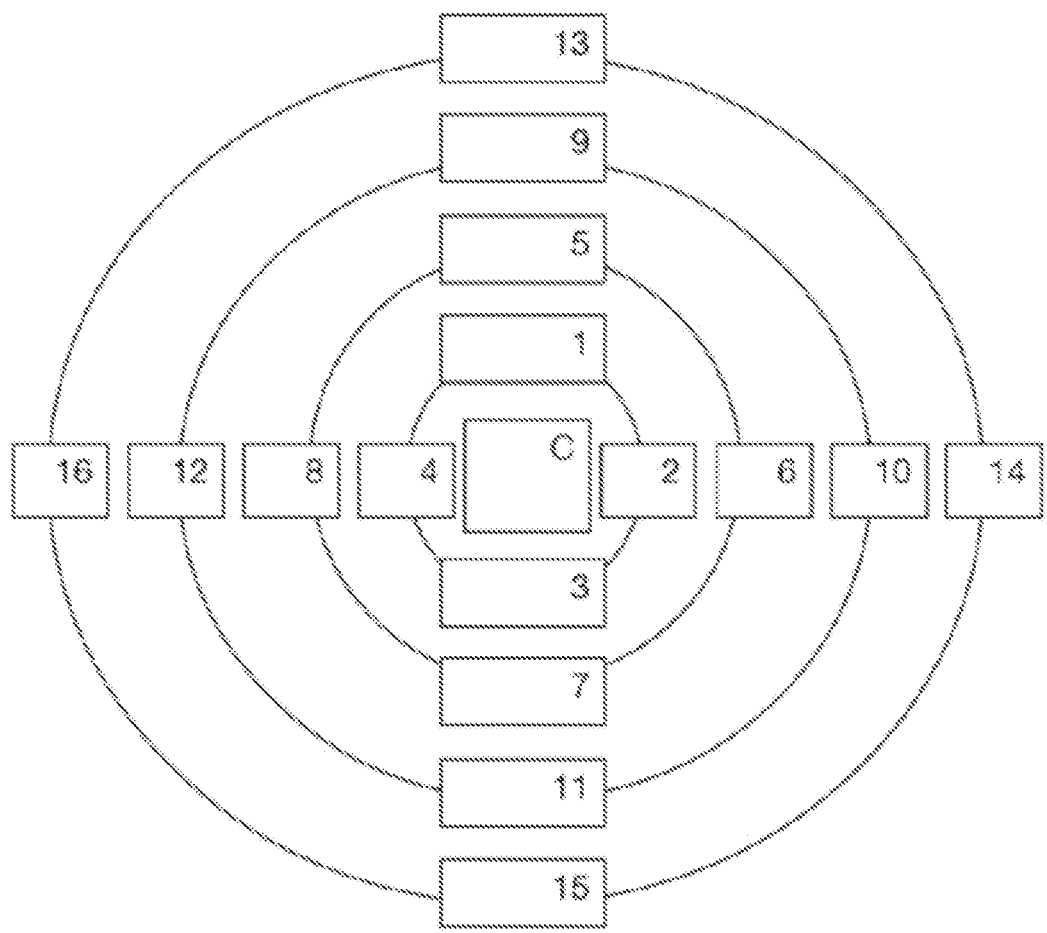
FIG. 1A—Sample SEM measurement locations according to protocol 003 in the prior art.

The present disclosure describes measurement of SEM values at and around healthy and damaged tissues, and the method of using the spatial variation in SEM measurements to evaluate and treatment of deep and early-stage pressure-induced injuries or ulcers.

This description is not intended to be a detailed catalog of all the different ways in which the disclosure may be implemented, or all the features that may be added to the instant disclosure. For example, features illustrated with respect to one aspect may be incorporated into other aspects, and features illustrated with respect to a particular aspect may be deleted from that aspect. Thus, the disclosure contemplates that in some aspects of the disclosure, any feature or combination of features set forth herein can be excluded or omitted. In addition, numerous variations and additions to the various aspects suggested herein will be apparent to those skilled in the art in light of the instant disclosure, which do not depart from the instant disclosure. In other instances, well-known structures, interfaces and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations, and variations thereof.

Unless otherwise defined, all technical and scientific term used herein have the same meaning as commonly understood by one of ordinary skill in the art to which this disclosure belongs. The terminology used in the description of the disclosure herein is for the purpose of describing particular aspects or aspects only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some aspects of the disclosure, any feature or combination of features set forth herein can be excluded or omitted.

The methods disclosed herein include and comprise one or more steps or actions for achieving the described method. The method steps and/or actions may be interchanged with one another without departing from the scope of the present invention. In other words, unless a specific order of steps or actions is required for proper operation of the aspect, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a SEM value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any aspect or aspect described as "exemplary" is not necessarily to be construed as preferred or advantageous over other aspects or aspects, nor is it meant to preclude equivalent structures and techniques known to those of ordinary skill in the art. Rather, use of the word exemplary is intended to present concepts in a concrete fashion, and the disclosed subject matter is not limited by such examples.

As used herein, the term "sub-epidermal moisture" or "SEM" refers to the amount of moisture in skin tissue under the epidermis. SEM may include intracellular and extracellular fluid. Without being bound by theory, when skin tissue is damaged, inflammation at the site of injury can cause blood vessels to dilate and increase blood flow into the skin tissue. There can also be an increase in blood vessel permeability, allowing fluid, proteins, and white blood cells to migrate from the circulation to the site of skin tissue damage. The flood of fluids, cells, and other substances to the injured site produces swelling and redness, and increases the amount of SEM in the damaged skin tissue. Processes like apoptosis and necrosis may also increase the amount of fluid in the damaged region.

As used herein, "tissue biocapacitance" refers to a biophysical marker for detecting tissue damage based on the increased level of fluids that build up in the interstitial space. Without being bound by theory, the greater the fluid content in a tissue, the higher the biocapacitance value. In some aspects, the methods described herein comprise a step of measuring the biocapacitance in a tissue. In some aspects, the methods described herein comprise a step of measuring the biocapacitance of the skin. In some aspects, the biocapacitance measured with the methods described herein vary linearly with the SEM in the tissue. In some aspects, the biocapacitance measured with the methods described herein vary non-linearly with the SEM in the tissue.

As used herein, "assessment of tissue health" refers to the quantitative or qualitative measurement of the condition of a tissue. In some aspects, assessment of tissue health is performed by a visual assessment. In some aspects, assessment of tissue health is performed by skin tissue assessment. In some aspects, assessment of tissue health is performed using electromagnetic energy. In some aspects, assessment of tissue health is performed by measuring one or more SEM values. In some aspects, assessment of tissue health is a risk analysis. In some aspects, assessment of tissue health is an analysis of the risk of developing a pressure sore or pressure ulcer. In some aspects, tissue health is measured by the Braden Scale. In some aspects, tissue health is measured by the Waterlow scale. In some aspects, assessment of tissue health is performed by at least one of a visual assessment, skin tissue assessment, Braden scale, Waterlow scale, and measurement of SEM values.

As used herein a "patient" may be a human or animal subject.

As used herein, "extracellular fluid" or "ECF" refers to bodily fluid contained outside of cells, including plasma, interstitial fluid, and transcellular fluid.

As used herein, "healthy" may describe skin tissue that does not exhibit symptoms of damage to cellular walls or blood vessels. Without being bound by theory, the presence of an increased amount of ECF may be an indication of such skin tissue damage.

As used herein, "damaged tissue" refers to tissue that is not healthy.

As used herein, an "erythema" refers to an area of superficial skin reddening. In some aspects, damaged tissue comprises an area of erythema.

As used herein, "region" or "target region" refers to an anatomical region on a subject. In some aspects, a region or target region is associated with an anatomical feature on a patient's body.

As used herein, "area," "tissue assessment area," or "assessment area" refers a subregion within an anatomical region. In some aspects, a tissue assessment area refers to a subregion outside and away from the damaged tissue. In some aspects, a tissue assessment area refers to a subregion at and around the damaged tissue. In some aspects, a tissue assessment area is an erythema. In some aspects, the boundary between different tissue assessment areas is delineated by an edge of an erythema.

As used herein, "location" or "measurement location" refers to a position where an SEM measurement is collected on a subject.

As used herein, "average" refers to taking the arithmetic mean of a set of numeric values. In an aspect, the numeric values can be SEM measurements.

As used herein, "cut-off", "cut-off value", "threshold", or "cut-off threshold" refers to a numeric value to which measured values or calculated values can be compared against for clinical utility.

As used herein, "spatially distinct locations" or "spatially distinct points" refers to two or more locations on a surface, for example, on a target region or assessment area, that do not overlap. In some aspects, two or more locations are spatially distinct if the areas of the two or more areas do not overlap. In some aspects, two or more locations are spatially distinct if the centers of the two or more areas do not overlap.

As used herein, "measurement time interval" refers to a period of time between two sets of SEM measurements. In some aspects, a measurement time interval is predetermined. In some aspects, a measurement time interval is a predetermined number of minutes. In some aspects, a measurement time interval is a predetermined number of hours. In some aspects, a measurement time interval is a predetermined number of days. In some aspects, a measurement time interval is a predetermined number of weeks. In some aspects, a measurement time interval is a predetermined number of months.

The present disclosure provides a system for assessing tissue health at and around a target region. In an aspect, the system comprises a device capable of making SEM measurements, including but not limited to that described in U.S. Pat. No. 9,398,879B2. In an aspect, the system comprises a device capable of making SEM measurements including but not limited to that described in U.S. Pat. No. 10,182,740B2. Both U.S. Pat. Nos. 9,398,879B2 and 10,182,740B2 are incorporated herein by reference in their entireties. In an aspect, the system comprises a device capable of making SEM measurements, including but not limited to the SEM Scanner Model 200 (Bruin Biometrics, LLC, Los Angeles, CA). In an aspect, the system comprises a device capable of making biocapacitance measurements. In an aspect, the system is configured to perform the methods described herein. In an aspect, the system comprises a processor. In an aspect, the system comprises a non-transitory computer-readable medium electronically coupled to the processor, and comprising instructions stored thereon that, when executed on the processor, perform the steps of the methods described herein.

In an aspect, the system comprises a device capable of making SEM measurements or biocapacitance measurements, the device comprising a coverlay. In an aspect, the coverlay may be a double-sided, copper-clad laminate and an all-polyimide composite of a polyimide film bonded to copper foil. In an aspect, the coverlay may comprise Pyralux 5 mil FR0150. Without being limited by theory, the use of this coverlay may avoid parasitic charges naturally present on the skin surface from interfering with the accuracy and precision of SEM measurements.

The present disclosure provides methods for assessing tissue health at and around a target region. In an aspect, a target region comprises one or more assessment areas. In an aspect, a target region comprises healthy tissue. In an aspect, a target region comprises damaged tissue. In an aspect, a target region comprises tissue suspected to be damaged.

One or more target regions on a body may be associated with an anatomical feature. In an aspect, anatomical features include, but are not limited to, the heel, lower back, sacrum, tailbone, hip, shoulder blade, ankle, elbow, ear, and the back of the head. In an aspect, a target region corresponds to an anatomical location or anatomical site (e.g., sacrum, heel, scapula, elbow, thoracic spine, trochanter, ischium, ear, or other fleshy tissue). In an aspect, a target region corresponds to a bony prominence.

In some aspects, a target region is the cranial region. In some aspects, a target region is the facial region. In some aspects, a target region is the frontal region. In some aspects, a target region is the orbital or ocular region. In some aspects, a target region is the buccal region. In some aspects, a target region is the auricle or otic region. In some aspects, a target region is the nasal region. In some aspects, a target region is the oral region. In some aspects, a target region is the mental region. In some aspects, a target region is the cervical region. In some aspects, a target region is the thoracic region. In some aspects, a target region is the mammary region. In some aspects, a target region is the sternal region. In some aspects, a target region is the abdominal region. In some aspects, a target region is the umbilical region. In some aspects, a target region is the coxal region (hip region). In some aspects, a target region is the pubic region. In some aspects, a target region is the inguinal or groin region. In some aspects, a target region is the pubic region. In some aspects, a target region is the femoral region. In some aspects, a target region is the patellar region. In some aspects, a target region is the crural region. In some aspects, a target region is the fibular region. In some aspects, a target region is the tarsal region. In some aspects, a target region is the pedal region. In some aspects, a target region is the digital/phalangeal region. In some aspects, a target region is the hallux. In some aspects, a target region is the axillary region. In some aspects, a target region is the brachial region. In some aspects, a target region is the antecubital region. In some aspects, a target region is the antebrachial region. In some aspects, a target region is the carpal region. In some aspects, a target region is the palmar region. In some aspects, a target region is the digital/phalangeal region. In some aspects, a target region is the pollex. In some aspects, a target region is the cervical region. In some aspects, a target region is the scapular region. In some aspects, a target region is the dorsal region. In some aspects, a target region is the lumbar region. In some aspects, a target region is the sacral region. In some aspects, a target region is the cervical region. In some aspects, a target region is the acromial region. In some aspects, a target region is the brachial region. In some aspects, a target region is the olecranal region. In some aspects, a target region is the antebrachial region. In some aspects, a target region is the manual or manus region. In some aspects, a target region is the gluteal region. In some aspects, a target region is the femoral region. In some aspects, a target region is the popliteal region. In some aspects, a target region is the sural region. In some aspects, a target region is the calcaneal region. In some aspects, a target region is the plantar region.

In an aspect, a tissue assessment area comprises an area or a volume in skin tissue where measurements of skin condition are made. In an aspect, an assessment area on a skin comprises an area on the surface of the skin. In an aspect, an assessment area on skin comprises an area on the surface of the skin and the volume of underlying skin tissue. In an aspect, an assessment area is an area on the skin centered over a PI/PU. In an aspect, an assessment area is an area on the skin centered over damaged tissue. In an aspect, an assessment area is an area on the skin centered over tissue suspected of having tissue damage. In an aspect, an assessment area is an area on the skin centered over tissue suspected of forming a PI/PU. In an aspect, an assessment area is an area on the skin centered over tissue at risk of forming a PI/PU. In an aspect, an assessment area is an area on the skin centered over skin with superficial reddening (erythema). In an aspect, an assessment area is circular. In an aspect, an assessment area is a ring. In an aspect, an assessment area is a rectangle. In an aspect, an assessment area is a ring centered over a pressure ulcer, with a radius or about 1 cm, about 2 cm, about 3 cm, about 4 cm, about 5 cm, about 6 cm, about 7 cm, about 8 cm, about 9 cm, or about 10 cm. In an aspect, an assessment area is a ring centered over damaged tissue, with a radius or about 1 cm, about 2 cm, about 3 cm, about 4 cm, about 5 cm, about 6 cm, about 7 cm, about 8 cm, about 9 cm, or about 10 cm. In an aspect, an assessment area is a ring centered over tissue suspected of having tissue damage, with a radius or about 1 cm, about 2 cm, about 3 cm, about 4 cm, about 5 cm, about 6 cm, about 7 cm, about 8 cm, about 9 cm, or about 10 cm. In an aspect, an assessment area is a ring centered over an erythema, with a radius or about 1 cm, about 2 cm, about 3 cm, about 4 cm, about 5 cm, about 6 cm, about 7 cm, about 8 cm, about 9 cm, or about 10 cm. In some aspects, a tissue measurement area may be the area of an erythema.

In an aspect, an edge of an erythema may be determined by visual inspection and standard skin and tissue assessment. In an aspect, an edge of an erythema may be determined by assessing the spatial variation in SEM measurements taken in a region. In an aspect, an edge of an erythema may be identified by a maximum value out of a set of SEM measurements.

An assessment area may comprise one or more measurement locations. One or more SEM measurements may be obtained at each measurement location. In an aspect, an assessment area comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or at least 20 measurement locations. In some aspects, a tissue assessment area comprises one, two, three, four, five, six, seven, eight, nine, ten, 11, 12, 13, 14, 15, 16, 17, 18, 19, or 20 measurement locations. In some aspects, a measurement location has an area that is the area in contact with an SEM measurement device. In some aspects, a measurement location is a point in the center of an area in contact with an SEM measurement device. In an aspect, a measurement location is spatially distinct from another measurement location.

In an aspect, measurement locations are in a spatially-specific pattern within the assessment area. In an aspect, measurement locations are randomly dispersed within the assessment area. In an aspect, the spatial pattern of measurement locations is readings is made in a pattern with a target region in the center. In an aspect, measurements are made in one or more circular patterns of increasing or decreasing size, cross-shaped patterns, T-shaped patterns, a set of specific locations, or randomly across a region. In an aspect, measurements may be taken at locations on one or more concentric circles centered on an anatomical region.

FIG. 1A illustrates an SEM measurement strategy in the prior art showing 17 spatially distinct measurement locations in one assessment area.

Figure 1B:
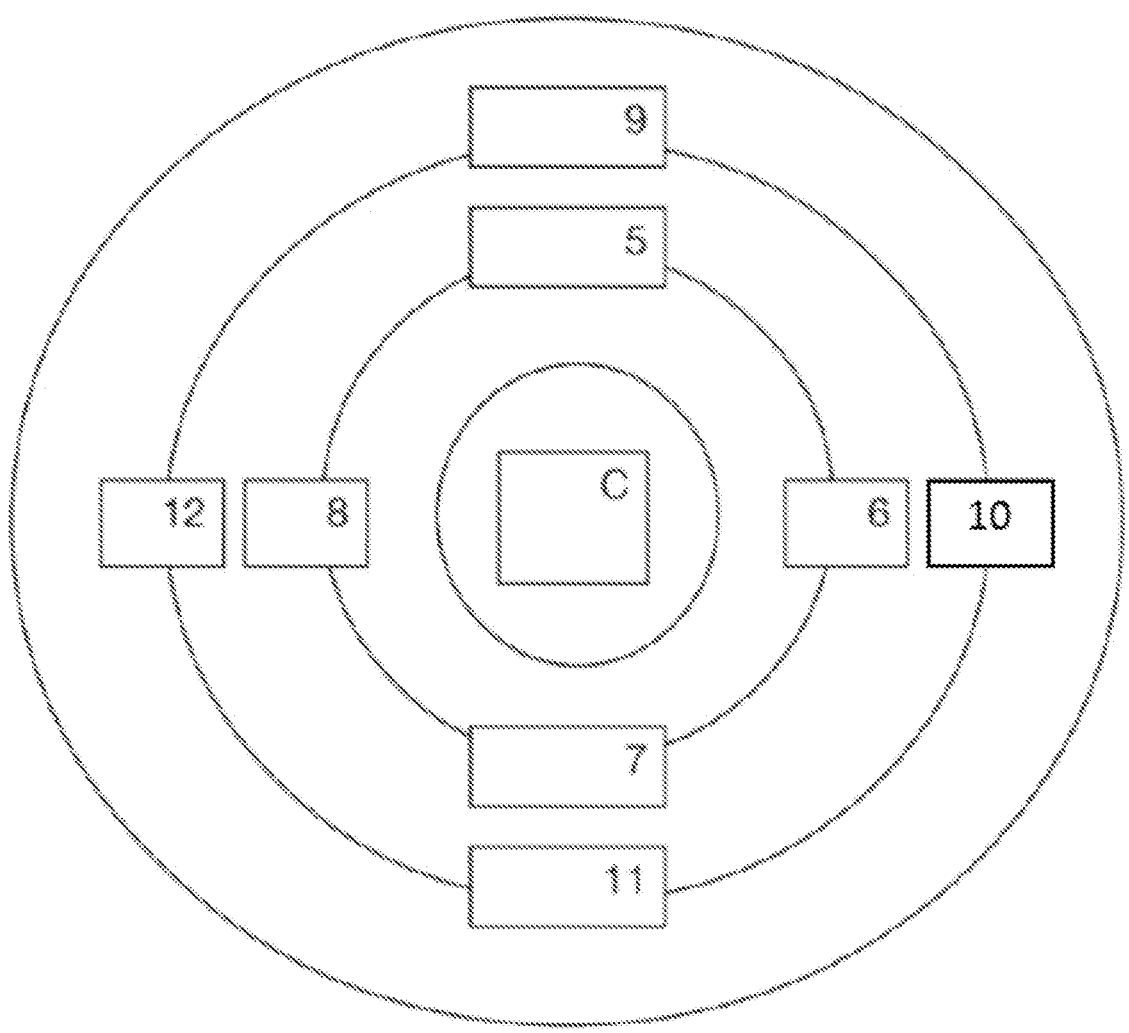
FIG. 1B—Sample SEM measurement locations according to protocol 004 in the prior art.

FIG. 1B illustrates another SEM measurement strategy in the prior art showing 9 spatially distinct assessment locations in one assessment area.

Figure 2A:
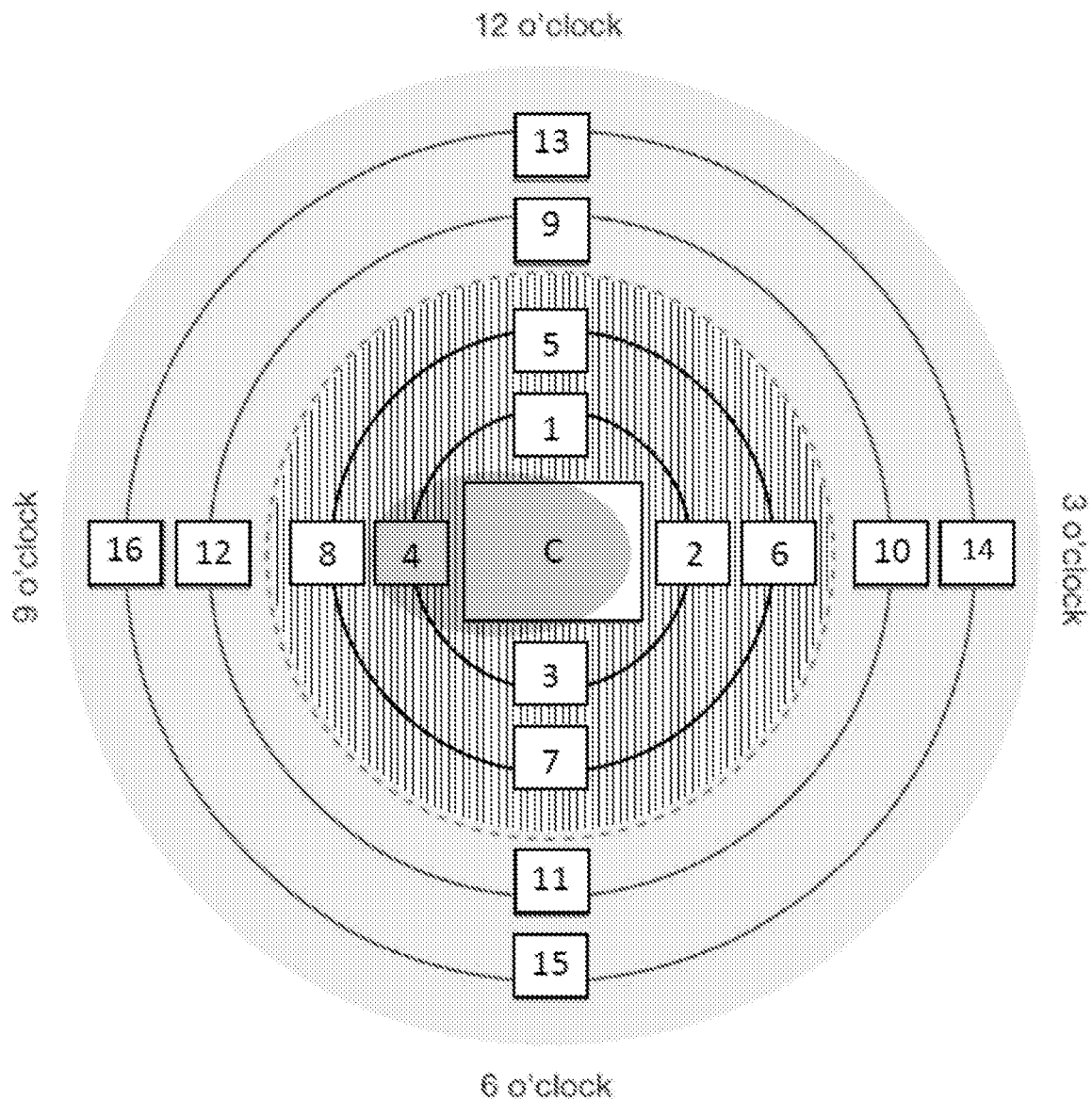
FIG. 2A—Sample SEM measurement locations in accordance with the methods in the present disclosure.

FIG. 2A illustrates an exemplary SEM assessment map for an exemplary algorithm ("Algorithm A") of this disclosure. In an aspect, the SEM measurement strategy comprises more than one assessment areas. In an aspect, a first assessment area is a circle with a first outer radius, e.g., as depicted by the dotted line in FIG. 2A. In an aspect, the center of a first assessment area 'C' comprises an area of damaged tissue, as depicted by the shaded oval in FIG. 2A. In an aspect, the center of a first assessment area 'C' is an area of damaged tissue. In an aspect, the center of a first assessment area 'C' is an area of tissue with suspected damage. In an aspect, the center of a first assessment area 'C' is centered over damaged tissue. In an aspect, the center of a first assessment area 'C' is an anatomical region, e.g., a heel, a sacrum. In an aspect, a second assessment area is an annulus with a second inner radius and a third outer radius centered on an anatomical region. In an aspect, a second assessment area is an annulus with a second inner radius and a third outer radius, centered around the first assessment area. In an aspect, a second assessment area is an annulus with a second inner radius and a third outer radius centered around an area of damaged tissue. In an aspect, a second assessment area is an annulus with a second inner radius and a third outer radius centered over damaged tissue. In an aspect, the second inner radius of the second assessment area, e.g., an annulus, is greater than the first outer radius of the first assessment area, e.g., a circle. In an aspect, the second inner radius of the second assessment area, e.g., an annulus, is equal to the first outer radius of the first assessment area, e.g., a circle. In an aspect, the first assessment area and the second assessment area do not overlap. In an aspect, a boundary between a first and a second assessment areas is delineated by an edge of an erythema. In an aspect, a boundary between a first and a second assessment areas is a circle that encompasses a region of damaged tissue within the circle. In an aspect, a boundary between a first and a second assessment areas is a circle that encompasses a region suspected to contain damaged tissue within the circle.

In an aspect, SEM measurements are obtained at locations along two lines that divide a circular assessment area into four quadrants, e.g., a first line at measurement locations 16, 12, 8, 4, 2, 6, 10, and 14, and a second line at measurement locations 15, 11, 7, 3, 1, 5, 9, and 13, as depicted in FIG. 2A. In an aspect, SEM measurements are obtained at locations in concentric rings within a circular assessment area, e.g., measurement locations 1, 2, 3, and 4, followed by measurement locations 5, 6, 7, and 8, as depicted in FIG. 2A. In an aspect, SEM measurements are obtained at locations along two lines that divide an annulus assessment area into four quadrants, e.g., a first line at measurement locations 16, 12, 8, 4, 2, 6, 10, and 14, and a second line at measurement locations 15, 11, 7, 3, 1, 5, 9, and 13, as depicted in FIG. 2A. In an aspect, SEM measurements are obtained at locations in concentric rings within an annulus assessment area, e.g., measurement locations 9, 10, 11, and 12, followed by measurement locations 13, 14, 15, and 16, as depicted in FIG. 2A.

In an aspect, the number of measurements taken within a first assessment area may be fewer than the number of measurements taken within a second assessment area. In an aspect, the number of measurements taken within a first assessment area may exceed the number of measurements taken within a second assessment area. In an aspect, the number of measurements taken within a first assessment area may equal to the number of measurements taken within a second assessment area. In an aspect, an average SEM value within a single assessment area is obtained from two, three, four, five, six, seven, eight, nine, ten, or more than ten SEM values measured in an assessment area.

In an aspect, a first plurality of SEM values are measured in the first assessment area, e.g., a circle with a first outer radius, at spatially distinct locations. In an aspect, a first plurality of SEM values are measured in the first assessment area, e.g., locations C, 1, 2, 3, 4, 5, 6, 7, and 8, as depicted in FIG. 2A. In an aspect, a first average SEM value is calculated as the arithmetic mean of the first plurality of SEM values. In an aspect, a second plurality of SEM values are measured in the second assessment area, e.g., an annulus with a second inner radius and a third outer radius, at spatially distinct locations. In an aspect, a second plurality of SEM values are measured in the second assessment area, e.g., locations 9, 10, 11, 12, 13, 14, 15, and 16, as shown in FIG. 2A. In an aspect, a second average SEM value is calculated as the arithmetic mean of the second plurality of SEM values. In an aspect, a first plurality of SEM values are measured in the first assessment area, e.g., a circle with a first outer radius, at spatially distinct locations, and a second plurality of SEM values are measured in the second assessment area, e.g., an annulus with a second inner radius and a third outer radius, at spatially distinct locations. In an aspect, a first average SEM value is calculated as the arithmetic mean of the first plurality of SEM values, and a second average SEM value is calculated as the arithmetic mean of the second plurality of SEM values. In an aspect, an SEM delta value is calculated as the difference between the first average SEM value and the second average SEM value. In an aspect, an SEM delta value is calculated as the difference between an average of the SEM measurements collected in the first assessment area, e.g., a circle, and an average of the SEM measurements collected in the second assessment area, e.g., an annulus.

In an aspect, the first plurality of SEM values are measured in the first assessment area, e.g., a circle with a first outer radius, at spatially distinct locations. In an aspect, the first plurality of SEM values are taken on a straight line across the first assessment area. In an aspect, the first plurality of SEM values are taken on a curved line within the first assessment area. In an aspect, the first plurality of SEM values are taken at locations on a specific pattern within the first assessment area. In an aspect, the measurement locations of the first plurality of SEM values are measured along 1, 2, 3, 4, 5, 6, 7, 8, 9, or 10 concentric circles within the first assessment area (circle). In an aspect, the measurement locations of the first plurality of SEM values are spatially separated from each other at a specified distance. In an aspect, the measurement locations of the first plurality of SEM values are about 0.5 cm, about 1 cm, about 1.5 cm, about 2 cm, about 2.5 cm, about 3.0 cm, about 3.5 cm, about 4.0 cm, about 4.5 cm, or about 5.0 cm apart. In an aspect, the measurement locations of the first plurality of SEM values are at least 0.5 cm, at least 1 cm, at least 1.5 cm, at least 2 cm, at least 2.5 cm, at least 3.0 cm, at least 3.5 cm, at least 4.0 cm, at least 4.5 cm, or at least 5.0 cm apart. In an aspect, the measurement locations of the first plurality of SEM values are at most 0.5 cm, at most 1 cm, at most 1.5 cm, at most 2 cm, at most 2.5 cm, at most 3.0 cm, at most 3.5 cm, at most 4.0 cm, at most 4.5 cm, or at most 5.0 cm apart.

In an aspect, the second plurality of SEM values are measured in the second assessment area, e.g., an annulus with a second inner radius and a third outer radius, at spatially distinct locations, are taken on a straight line across the second assessment area. In an aspect, the second plurality of SEM values are taken on a curved line within second first assessment area. In an aspect, the second plurality of SEM values are taken at locations on a specific pattern within the second assessment area. In an aspect, the measurement locations of the second plurality of SEM values are measured along 1, 2, 3, 4, 5, 6, 7, 8, 9, or 10 concentric circles within the second assessment area (annulus). In an aspect, the measurement locations of the second plurality of SEM values are spatially separated from each other at a specified distance. In an aspect, the measurement locations of the second plurality of SEM values are about 0.5 cm, about 1 cm, about 1.5 cm, about 2 cm, about 2.5 cm, about 3.0 cm, about 3.5 cm, about 4.0 cm, about 4.5 cm, or about 5.0 cm apart. In an aspect, the measurement locations of the second plurality of SEM values are at least 0.5 cm, at least 1 cm, at least 1.5 cm, at least 2 cm, at least 2.5 cm, at least 3.0 cm, at least 3.5 cm, at least 4.0 cm, at least 4.5 cm, or at least 5.0 cm apart. In an aspect, the measurement locations of the second plurality of SEM values are at most 0.5 cm, at most 1 cm, at most 1.5 cm, at most 2 cm, at most 2.5 cm, at most 3.0 cm, at most 3.5 cm, at most 4.0 cm, at most 4.5 cm, or at most 5.0 cm apart.

In an aspect, a target region is flagged as containing damaged tissue when the SEM delta value calculated for the target region is equal to or greater than a predetermined threshold. In an aspect, a predetermined threshold is about 0.6, about 0.65, about 0.7, about 0.75, about 0.8, about 0.85, about 0.9, about 0.95, or about 1.0. In an aspect, a predetermined threshold is at least 0.6, at least 0.65, at least 0.7, at least 0.75, at least 0.8, at least 0.85, at least 0.9, at least 0.95, or at least 1.0. In an aspect, each target region of a plurality of target regions has a different threshold. In an aspect, all target regions on the same patient has the same threshold. In an aspect, two or more target regions have the same threshold. It will be understood that the predetermined threshold is not limited by design, but rather, one of ordinary skill in the art would be capable of choosing a predetermined value based on a given SEM delta value, and based on the specific anatomical regions where the measurements were performed.

In an aspect, the method according to the present disclosure does not require determining a maximum SEM value or a minimum SEM value from SEM values measured at and around an anatomical region. In an aspect, the method according to the present disclosure does not require determining a maximum average SEM value from a plurality of average SEM values. In an aspect, the method according to the present disclosure does not require determining a difference between the maximum average SEM value and each of the average SEM values measured around an anatomical region.

In an aspect, the criteria wherein a tissue is flagged as containing damaged tissue have both a spatial and a chronological component. In an aspect, the criteria wherein a tissue is flagged as containing damaged tissue has a spatial component when the SEM delta values are calculated from a predetermined set of measurement locations within a target region, e.g., measurement locations as shown in FIG. 2A. In an aspect, the criteria wherein a tissue is flagged as containing damaged tissue has a chronological component when the SEM delta values are calculated from a predetermined portion of a time interval. In an aspect, a set of SEM measurements is taken at regular intervals separated by a measurement time interval. In an aspect, a set of SEM measurements comprises one or more measurements taken at one or more locations in a measurement map. In an aspect, a set of SEM measurements comprises one or more measurements taken at each location in a measurement map, such as but not limited to a map as illustrated in FIG. 2A. In an aspect, a set of SEM measurements comprises one or more measurements taken at a subset of locations in a measurement map. In an aspect, a set of SEM measurements are taken every hour, every 2 hours, every 3 hours, every 4 hours, every 5 hours, every 6 hours, every 7 hours, every 8 hours, every 9 hours, every 10 hours, every 11 hours, every 12 hours, every 13 hours, every 14 hours, every 15 hours, every 16 hours, every 17 hours, every 18 hours, every 19 hours, every 20 hours, every 21 hours, every 22 hours, or every 23 hours. In an aspect, SEM measurements are taken every day, every 2 days, every 3 days, every 4 days, every 5 days, or every 6 days. In an aspect, a set of SEM measurements are taken every week, every 2 weeks, every 3 weeks, every 4 weeks, every 5 weeks or every 6 weeks. In an aspect, a set of SEM measurements are taken every month, every 2 months, every 3 months, every 4 months, every 5 months, every 6 months, every 7 months, every 8 months, every 9 months, or every 10 months. In an aspect, a first set of SEM measurements taken at a first timepoint may comprise a different number of SEM measurements as a second set of SEM measurements taken at a second timepoint in the time interval. In an aspect, a first set of SEM measurements taken at a first timepoint may comprise the same number of SEM measurements as a second set of SEM measurements taken at a second timepoint in the time interval. In an aspect, a first set of SEM measurements taken at a first timepoint comprises measurements from a first subset of locations in a measurement map and a second set of SEM measurements comprises measurements from a second subset of locations in a measurement map, wherein the first and second subset of locations are not the same. In an aspect, a first set of SEM measurements comprises measurements from a first subset of locations in a measurement map and a second set of SEM measurements comprises measurements from a second subset of locations in a measurement map, wherein the first and second subset of locations are the same.

In an aspect, a tissue is flagged as containing damaged tissue when the SEM delta values calculated from at least X sets of measurements out of Y consecutive sets of measurements are equal or greater than the predetermined threshold. In an aspect, at least X measurements is at least 1 set of measurement, at least 2 sets of measurements, at least 3 sets of measurements, at least 4 sets of measurements, at least 5 sets of measurements, at least 6 sets of measurements, at least 7 sets of measurements, at least 8 sets of measurements, or at least 9 sets of measurements. In an aspect, Y consecutive sets of measurements is 2 consecutive sets of measurements, 3 consecutive sets of measurements, 4 consecutive sets of measurements, 5 consecutive sets of measurements, 6 consecutive sets of measurements, 7 consecutive sets of measurements, 8 consecutive sets of measurements, 9 consecutive sets of measurements, or 10 consecutive sets of measurements. In an aspect, the predetermined portion of a time interval may be defined as some portion of a different specific time period (weeks, month, hours etc.). In an aspect, a tissue is flagged as containing damaged tissue when the SEM delta values calculated from at least X days out of Y consecutive days of measurements are equal or greater than the predetermined threshold. In an aspect, at least X days is at least 1 day, at least 2 days, at least 3 days, at least 4 days, at least 5 days, at least 6 days, at least 7 days, at least 8 days, or at least 9 days. In an aspect, Y consecutive days is 2 consecutive days, 3 consecutive days, 4 consecutive days, 5 consecutive days, 6 consecutive days, 7 consecutive days, 8 consecutive days, 9 consecutive days, or 10 consecutive days. In an aspect, a tissue is flagged as containing damaged tissue when the SEM delta values calculated from at least X hours out of Y consecutive hours of measurements are equal or greater than the predetermined threshold. In an aspect, at least X hours is at least 1 hour, at least 2 hours, at least 3 hours, at least 4 hours, at least 5 hours, at least 6 hours, at least 7 hours, at least 8 hours, or at least 9 hours. In an aspect, Y consecutive hours is 2 consecutive hours, 3 consecutive hours, 4 consecutive hours, 5 consecutive hours, 6 consecutive hours, 7 consecutive hours, 8 consecutive hours, 9 consecutive hours, or 10 consecutive hours. In an aspect, a tissue is flagged as containing damaged tissue when the SEM delta values calculated from at least X weeks out of Y consecutive weeks of measurements are equal or greater than the predetermined threshold. In an aspect, at least X weeks is at least 1 week, at least 2 weeks, at least 3 weeks, at least 4 weeks, at least 5 weeks, at least 6 weeks, at least 7 weeks, at least 8 weeks, or at least 9 weeks. In an aspect, Y consecutive weeks is 2 consecutive weeks, 3 consecutive weeks, 4 consecutive weeks, 5 consecutive weeks, 6 consecutive weeks, 7 consecutive weeks, 8 consecutive weeks, 9 consecutive weeks, or 10 consecutive weeks. In an aspect, a tissue is flagged as containing damaged tissue when the SEM delta values calculated from at least X months out of Y consecutive months of measurements are equal or greater than the predetermined threshold. In an aspect, at least X months is at least 1 month, at least 2 months, at least 3 months, at least 4 months, at least 5 months, at least 6 months, at least 7 months, at least 8 months, or at least 9 months. In an aspect, Y consecutive months is 2 consecutive months, 3 consecutive months, 4 consecutive months, 5 consecutive months, 6 consecutive months, 7 consecutive months, 8 consecutive months, 9 consecutive months, or 10 consecutive months.

In an aspect, surface moisture and matter above a patient's skin surface may be removed prior to the measuring step. In an aspect, the measuring step may take less than one second, less than two seconds, less than three seconds, less than four seconds, or less than five seconds.

In an aspect, a quality metric may be generated for any plurality of measurements. In an aspect, a quality metric as used herein refers to standards for measuring the repeatability, consistency, precision, or accuracy of SEM measurements. Without being bound by theory, the repeatability, consistency, precision, or accuracy of SEM measurements can be affected by many factors, including but not limited to the anatomical region of the measurement, the skill of the clinician, or the skin condition of the patient. In an aspect, the quality metric is a measure of the repeatability of the measurements. In an aspect, the quality metric is a measure of the skill of the clinician that took the measurement. In an aspect, the quality metric includes one or more statistical parameters, including but not limited to an average, a mean, a standard deviation, a z-factor, or a p-value. In an aspect, a quality metric may be generated for any plurality of measurements made within the same patient. In an aspect, a quality metric may be generated for any plurality of measurements made across different patients. In an aspect, the quality metric includes a comparison of individual measurements to a predetermined value. In an aspect, the quality metric includes a comparison of individual measurements to a predetermined value for that particular measurement location. In an aspect, the quality metric includes a comparison of individual measurements to a predetermined value for healthy tissue. In an aspect, the quality metric includes a comparison of individual measurements to a predetermined value for damaged tissue. In an aspect, the quality metric includes a comparison of individual measurements to a predefined range. In an aspect, the quality metric includes a comparison of individual measurements to a predefined range determined for that particular measurement location. In an aspect, the quality metric includes a comparison of individual measurements to a predefined range determined for healthy tissue. In an aspect, the quality metric includes a comparison of individual measurements to a predefined range determined for damaged tissue.

In an aspect, evaluating a patient further comprises using a remote device, such as a computer, laptop computer, smart phone, tablet or other mobile or wearable device. In an aspect, the remote device is configured for intermittent monitoring. In an aspect, the remote device is configured for constant monitoring. In an aspect, the remote device communicates wirelessly with a SEM measurement apparatus, for example a SEM scanner that comprises the capability to wirelessly communicate with a WiFi access point. In an aspect, the remote device communicates wirelessly with a SEM measurement apparatus via Bluetooth. In an aspect, the remote device is carried by the user of the SEM measurement apparatus. In an aspect, information received from the SEM measurement apparatus is stored in a database. In an aspect, information received from the SEM measurement apparatus for a patient is transferred over a network to another server that stores a portion of the information in an electronic medical record (EMR) of the patient. In an aspect, information from the SEM measurement apparatus or retrieved from the database or EMR is transferred to an external server and then to a computer, for example a computer at the office of a doctor who is providing care for the patient.

The present disclosure provides a system for assessing tissue health at and around a target region and flagging tissue as containing damaged tissue. In an aspect, the user inputs an approximate target region, e.g., heel or sacrum, into the device through a graphical user interface (GUI). In an aspect, the user inputs other information about the patient, e.g., demographic or health information, into the device through a GUI. In an aspect, the system determines the ideal measurement locations using the methods described in the present disclosure. In an aspect, the system determines the ideal measurement locations based in part on the target region inputted by the user. In an aspect, the system determines the ideal measurement locations based in part on the demographic information of the patient inputted by the user, e.g., age or gender. In an aspect, the system determines the ideal measurement locations based in part on other health information of the patient inputted by the user, e.g., age or gender. In an aspect, the system displays a map of measurement locations on a GUI. In an aspect, the system guides a user to take measurements at specific locations based on a map of measurement locations displayed on a GUI, the map of measurement locations being determined by the methods described herein. In an aspect, the system assigns each SEM measurement to a specific location on the map of measurement locations when it is taken. In an aspect, the system assigns each SEM measurement to a specific measurement time in a specific time period when measurements are taken. In an aspect, the system calculates SEM delta values based on the methods described herein. In an aspect, the system determines whether a tissue is flagged as containing damaged tissue according to the methods and criteria described herein. In an aspect, the system determines whether a tissue is flagged as containing damaged tissue based on the spatial component of the criteria, e.g., specific measurement locations. In an aspect, the system determines whether a tissue is flagged as containing damaged tissue based on the chronological component of the criteria, e.g., at least X measurements with SEM delta values equal or greater than the predetermined threshold within Y consecutive measurements. In an aspect, the system flags the tissue as containing damaged tissue by displaying a message or icon on the GUI. In an aspect, the system flags the tissue as containing damaged tissue by producing a sound, e.g., a beep or alarm. In an aspect, the system determines the specific location on the map of measurement locations that contains damaged tissue, according to the methods described herein. In an aspect, the system displays on the GUI the specific location that contains damaged tissue on the map of measurement locations.

In an aspect, the method further comprises performing an assessment using one or more objective measurements selected from the group consisting of: sub-epidermal moisture, bioimpedance, blood perfusion, biocapacitance, blood oxygenation, pressure measurement; capillary pressure, magnetic resonance imaging, thermal imaging, spectral imaging, ultrasound imaging, transcutaneous water loss, and detection of interleukin-1 alpha presence at one or more anatomical region of interest. In an aspect, the method further comprises performing an assess using blood perfusion, including but not limited to the methods described in U.S. Patent Publication No. US 2020/0015735 A1. In an aspect, the method further comprises performing an assessment using ultrasound, including but not limited to the methods described in International Patent Publication No. WO 2021/096992 A1. In an aspect, the method further comprises performing an assessment using capillary pressure measurements, including but not limited to the methods described in International Patent Publication No. WO 2021/096994 A1. In an aspect, the method further comprises performing an assessment using positron emission tomography imaging, including but not limited to the methods described in International Patent Publication No. WO 2021/096993. In an aspect, the method further comprises performing an assessment using thermal imaging, including but not limited to the methods described in International Patent Publication No. WO 2021/097081 A1. In an aspect, the method further comprises performing an assessment using spectral imaging, including but not limited to the methods described in International Patent Publication No. WO 2021/097079 A1. In an aspect, the method further comprises performing an assessment that measures transepidermal water loss, including but not limited to the methods described in International Patent Publication No. WO 2021/097037 A1. In an aspect, the method further comprises performing an assessment that detects the local interleukin-1 alpha level, including but not limited to the methods described in International Patent Publication No. WO 2021/097083 A1. In an aspect, the method further comprises performing an assessment using magnetic resonance imaging, including but not limited to the methods described in International Patent Publication No. WO 2021/097033 A1. In an aspect, the method further comprises performing an assessment using pressure measurements, including but not limited to the methods described in International Patent Publication No. WO 2021/096996 A1. All of U.S. Patent Publication No. US 2020/0015735 A1, and International Patent Publication Nos. WO 2021/096992 A1, WO 2021/096994 A1, WO 2021/096993 A1, WO 2021/097081 A1, WO 2021/097079 A1, WO 2021/097037 A1, WO 2021/097083 A1, WO 2021/097033 A1, WO 2021/096996 A1, U.S. Pat. Nos. 9,398,879 B2 and 10,182,740 B2 are incorporated herein by reference in their entireties.

Having now generally described the invention, the same will be more readily understood through reference to the following examples that are provided by way of illustration, and are not intended to be limiting of the present disclosure, unless specified.

EXAMPLES

Example 1: Study Procedure for Clinical Trial Evaluating the Use of Spatial Variation in SEM Values to Determine Damaged Tissue for Clinical Intervention Subjects with Stage I or Stage II PI/PU or a suspected deep tissue injury (sDTI) (Arm I) were recruited under protocol 003 and healthy subjects unaffected by PI/PUs (Arm II) were recruited under protocol 004. For the PI/PU arm (Arm I), all enrolled subjects were residents of nursing homes or similar care facilities with a Stage I or Stage II PI/PU or an sDTI (suspected deep tissue injury) as confirmed by visual assessment and clinical judgment by the principal investigator and trained, experienced facility staff. All subjects met inclusion/exclusion criteria as outlined in Table 1. Expert investigators and PI/PU HCPs evaluating all subjects were trained in SEM measurements but blinded to clinical interpretations of SEM readings. Diagnosis of patient condition was confirmed by expert physicians after detailed assessments and diagnosis by specialists. Principal investigators were responsible for final decisions made with tie-breaker diagnosis.

TABLE 1

INCLUSION/EXCLUSION CRITERIA FOR ARM I AND ARM II

| Arm I: Protocol 003 | Arm II: Protocol 004 |
|---|---|
| Inclusion criteria | Inclusion criteria |
| 1. Subjects ≥55 years of age | 1. Subjects ≥55 years of age |
| 2. Subject or proxy is willing and able to provide informed consent | 2. Subject or proxy is willing and able to provide informed consent |
| 3. Subject is agreeable to having skin assessments and SEM readings performed | 3. Subject is agreeable to having skin assessments and SEM readings performed |
| 4. Subject has a PI/PU (Stage I or II, or suspected DTI) | |
| Exclusion criteria | Exclusion criteria |
| 1. Subject has broken skin at the wound site | 1. Subject has broken skin at the anatomical locations being assessed |
| 2. Subjects for whom the physical act of performing inspections and readings required in this study are contra-indicated | 2. Subjects with limited physical capacity or accessibility to the anatomical locations that would prohibit clinical evaluations and measurements to be performed. |
| 3. Subjects for whom none of the anatomical sites where the pressure injuries are located are evaluable. | |
| 4. Subject has pressure injuries on the face and head | 3. Subjects or legal representatives who are unable to understand the aims and objectives of the study. |
| 5. Subjects or legal representatives who are unable to understand the aims and objectives of the trial | 4. Presence of any condition(s) that seriously compromise the subject's ability to complete this study. |
| 6. Presence of any condition(s) which seriously compromises the subject's ability to complete this study | 5. Subject has been told by a physician that he/she has any one of the following: rheumatoid arthritis, gout or an autoimmune disorder. |
| 7. Subject is Comfort Measure Only (CMO) status | |
| 8. Subject is pregnant | 6. Subject is on systemic or topical corticosteroids. Subjects using topical |
| 9. Subject is incarcerated | |

TABLE 1-continued

INCLUSION/EXCLUSION CRITERIA FOR ARM I AND ARM II

| Arm I: Protocol 003 | Arm II: Protocol 004 |
|---|---|
| 10. Subject has participated in a clinical trial within the last 30 days | corticosteroids are excluded only if medication is placed on any of the anatomical locations being assessed |

DTI—deep tissue injury;
PI/PU—pressure injury or ulcer;
SEM—sub-epidermal moisture A total of 175 subjects were enrolled: 59 subjects with PI/PUs on the heel (33.7%); 63 subjects with PI/PUs on the sacrum (36%); three subjects with PI/PUs on the thoracic spine, right trochanter and right ischium (1.7%), one each, respectively; and 50 subjects unaffected by PI/PUs (28.6%).

STAs performed at the site of PI/PU, and sacrum and heels for healthy subjects included:
  Evaluation of erythema
  PI/PU stage classification
  Complete Braden scale or skin type question of the Waterlow scale completed to assess an individual subject's PI/PU risk and skin quality, respectively
  Pain at the anatomical site of the PI/PU using a patient-reported analogue scale (no pain to worst pain, 0-10)
  Systemic oedema
  Calluses
  Scar tissue
  Blisters All required assessments were performed in a single study visit for both arms.

Consent, screening and enrolment occurred on the same day as/or prior to the assessments. Demographic/physical characteristics collected at the time of the assessment included:
  Date of birth, gender, race and ethnicity
  Height and weight
  Primary and secondary admission diagnoses, admission unit, bed type and daily functional status, as well as living situation prior to admission, were collected as indicators of functional status and considered as potential confounders or stratifying factors. Pertinent medical history for each study subject, such as select comorbidities, medications and prior history of PI/PU, were collected as these factors may impact risk of PI/PU development or SEM readings. There were no protocol deviations due to inclusion/exclusion criteria or withdrawal criteria.

Example 2: Procedure for Taking SEM Readings

A PI/PU was defined as per NPUAP 2014 guidelines (consistent with NPIAP 2019 guidelines) as a localised injury to the skin and/or underlying tissue, usually over a bony prominence, as a result of pressure, or pressure in combination with shear. The discolored tissue consisted of the reddened tissue, also known as erythema of the PI/PU, or the purple/maroon tissue of the sDTI. The periwound region was defined as a region not exhibiting signs of any PI/PU as per expert STA. All readings were taken spatially in the region of the bony prominence of S4 for the sacral regions and at the calcaneus for heels.

Minor modifications to the protocol were approved by the IRB before subject enrollment in Arm II; for example, principal investigators requested not to include the 'Southern' readings due to modesty concerns of sacral assessments.

Example 3: Algorithms for Evaluating the Spatial Variation in SEM Readings

Figure 2B:
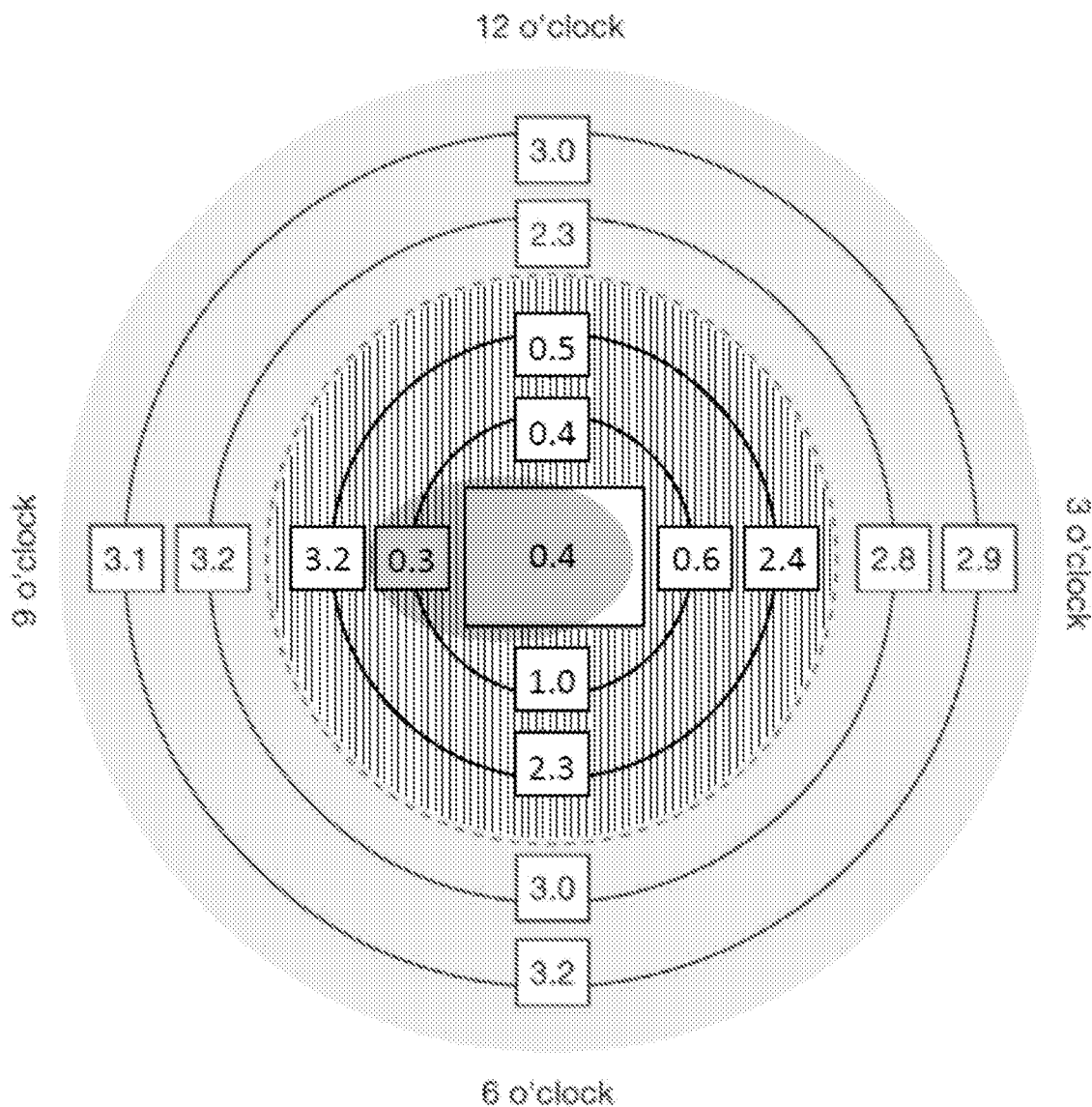
FIG. 2B—Sample SEM measurement results obtained in accordance with the methods in the present disclosure, represented as an SEM map.
Figure 3:
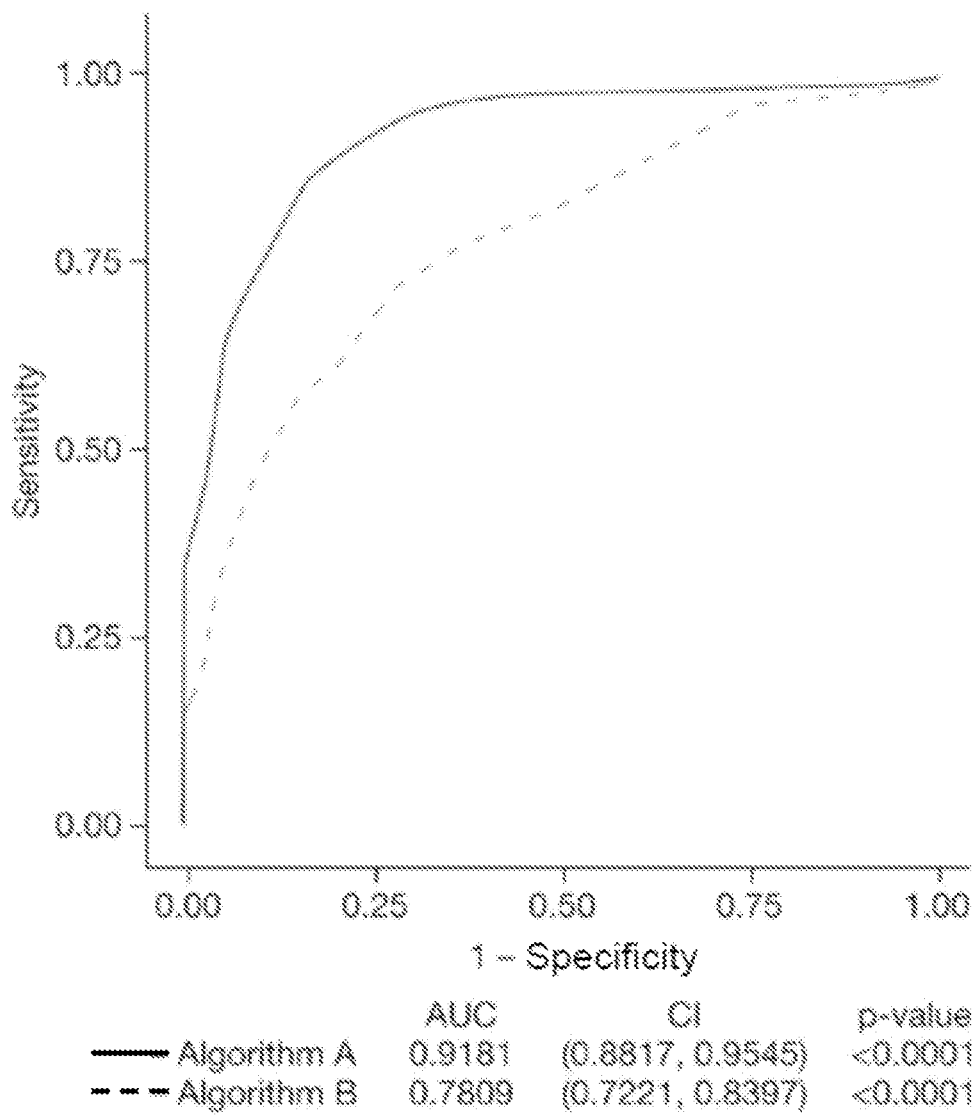
FIG. 3—Receiver operating characteristics (ROC) curve illustrating diagnostic sensitivity and specificity in detecting pressure ulcer/injury relative to skin and tissue assessment using the methods in the present disclosure.

Mathematical models developed post hoc, based on spatial SEM readings, resulted in two algorithms: the first derived from 17 assessment points (Algorithm A) for Arm I subjects (FIG. 2B), the second from six sacral and four heel assessment points for Arm II subjects (Algorithm B). Algorithm A calculated SEM delta as a difference of the average spatial SEM readings outside of the subject's erythema (rings 2-4) and the average SEM readings between the center and ring 1. Algorithm B calculated SEM delta as a difference between the lowest and highest absolute spatial SEM readings for a specific anatomy. Sensitivity and specificity tables were calculated for a range of cut-off values as per the statistical plan.

Example 4: Statistical Analysis for Evaluating the Sensitivity, Specificity, and Clinical Utility of Algorithms for Evaluating the Spatial Variation in SEM Readings The all subject population, the safety population, the intent-to-treat (ITT) population and the per protocol population were all identical. Therefore, all tabulations and analyses were performed on and reported for the ITT population. Statistical analyses were performed in R Core Team 2013 (R Foundation, Vienna, Austria) and confirmed in JMP (SAS Institute, Cary, NC) or performed in SAS 9.4 (SAS Institute, Cary, NC). All statistical comparisons were carried out at the two-sided 5% level of significance by an independent biostatistician. Sensitivity and specificity were calculated based on counts of true positive (TP), true negative (TN), false positive (FP) and false negative (FN) findings as defined by the US FDA such that:

$\text{Sensitivity} = 100 \times TP/(TP+FN)$ $\text{Specificity} = 100 \times TN/(FP+TN)$ Receiver operating characteristic (ROC) curve analysis computes and graphically displays all combinations of sensitivity and specificity. Resulting values of 'area under the curve' (AUC) range from 0 to 1 (0-100%), with a 45° intercept representing the line of randomness (0.5/50% sensitivity and specificity represents randomness). Diagnostic certainty for the test increases with values above 0.5.

Example 5: Demographic Information of the Study Population

One hundred and seventy-five participants (44.6% (n=78) male and 55.4% (n=97) female) were enrolled from 16 sites in the US (53% (n=93) VB and 47% (n=82) LA). All enrolled subjects completed the study. For Arm I, there were 38 procedural protocol deviations (LA: n=4; VB: n=34) related to missing SEM readings in the gluteal cleft— subjects' concerns regarding modesty being the reason. Additionally, there were 27 procedural protocol deviations (VB) related to missing date of PI/PU diagnosis where the nursing facility often did not record the initial date in their records. Missing demographic data were noted for age (n=1), race (n=2) and BMI (n=3). Neither type of procedural deviations affected study results. There were no protocol deviations in Arm II. Missing data for race were noted in two subjects. A detailed description of patient demographics is provided in Table 2.

TABLE 2

SUBJECT DEMOGRAPHICS

|  | Arm I (affected) | Arm II (unaffected) | p-value* |
|---|---|---|---|
| Age (years) | | | |
| n | 124 | 50 | <0.0001 |
| Mean (standard deviation) | 82.68 (10.875) | 66.8 (7.282) | |
| Median (minimum, maximum) | 85 (48, 99) | 66 (55, 82) | |
| Gender, n (%) | | | |
| Female | 72 (57.6%) | 25 (50%) | 0.402 |
| Male | 53 (42.4%) | 25 (50%) | |
| Race, n (%) | | | |
| Non-white | 39 (31.2%) | 9 (18%) | 0.1289 |
| White | 84 (67.2%) | 39 (78%) | |
| Ethnicity, n (%) | | | |
| Hispanic or Latino | 9 (7.2%) | 1 (2%) | 0.2851 |
| Not Hispanic or Latino | 116 (92.8%) | 49 (98%) | |
| BMI (kg/m$^2$) | | | |
| n | 122 | 50 | <0.0001 |
| Mean (standard deviation) | 23.53 (6.429) | 29.57 (6.854) | |
| Median (minimum, maximum) | 22.8 (12.6, 62.4) | 28.15 (19.7, 49.1) | |

*p-values comparing affected and unaffected subjects were generated using Fisher's Exact test for categorical variables. p-values comparing affected and unaffected subjects were generated using an independent sample t-test with a Satterthwaite correction in the cases where the variances were not statistically equal for continuous variables.

Example 6: Pressure Injury/Ulcer Characteristics of Study Subjects

In Arm I, all enrolled subjects were evaluated at a single anatomical (PI/PU) location except for four subjects who presented with PI/PUs on both heels and were assessed at both heels. Therefore, Arm I enrolled 125 subjects and assessed 129 PI/PUs, 42.6% Stage I PI/PUs (n=55), 2.3% Stage II PI/PUs (n=3) and 55% sDTIs (n=71). Table 3 summarises the PI/PU stages and wound characteristics. STA results are summarised in Table 4.

TABLE 3

PRESSURE INJURY/ULCER (PI/PU) CHARACTERISTICS OF STUDY SUBJECTS (ARM I)

|  | Subjects with heel wounds (n = 63 wounds on 59 subjects) | Subjects with sacral wounds (n = 66 wounds on 66 subjects) | All (n = 129 wounds on 125 subjects) |
|---|---|---|---|
| PI/PU stage, n (%) | | | |
| None | 0 | 0 | 0 |
| Stage 1 | 13 (20.6%) | 42 (63.6%) | 55 (42.6%) |
| Stage 2 | 0 | 3 (4.5%) | 3 (2.3%) |
| Stage 3 or 4 | 0 | 0 | 0 |
| Unstageable | 0 | 0 | 0 |
| Suspected deep tissue injury | 50 (79.4%) | 21 (31.8%) | 71 (55%) |
| Characteristics of wound edges, n (%) | | | |
| Indistinct, diffuse, none clearly visible | 25 (42.4%) | 48 (72.7%) | 73 (58.4%) |
| Distinct, outline clearly visible, attached, even with wound base | 29 (49.2%) | 15 (22.7%) | 44 (35.2%) |
| Well-defined, not attached to wound base | 3 (5.1%) | 2 (3%) | 5 (4%) |
| Well-defined, not attached to base, | 0 | 1 (1.5%) | 1 (0.8%) |

TABLE 3-continued

PRESSURE INJURY/ULCER (PI/PU) CHARACTERISTICS
OF STUDY SUBJECTS (ARM I)

| | Subjects with heel wounds (n = 63 wounds on 59 subjects) | Subjects with sacral wounds (n = 66 wounds on 66 subjects) | All (n = 129 wounds on 125 subjects) |
|---|---|---|---|
| rolled under, thickened | | | |
| Missing | 2 (3.4%) | 0 | 2 (1.6%) |
| Recurring wound? n (%) | | | |
| No | 49 (83.1%) | 59 (89.4%) | 108 (86.4%) |
| Yes | 8 (13.6%) | 7 (10.6%) | 15 (12%) |
| Missing | 2 (3.4%) | 0 | 2 (1.6%) |

TABLE 4

SKIN AND TISSUE ASSESSMENT (STA)
RESULTS OF STUDY SUBJECTS (ARM I)

| | Subjects with heel wounds (n = 59) | Subjects with sacral wounds (n = 66) | All (n = 125) |
|---|---|---|---|
| Braden scale total score categories, n (%) | | | |
| Very high risk: Total Score 9 or less | 6 (10.2%) | 13 (19.7%) | 19 (15.2%) |
| High risk: Total score 10-12 | 14 (23.7%) | 28 (42.4%) | 42 (33.6%) |
| Moderate risk: Total score 13-14 | 11 (18.6%) | 10 (15.2%) | 21 (16.8%) |
| Mild risk: Total score 15-18 | 23 (39.0%) | 13 (19.7%) | 36 (28.8%) |
| No risk: Total score 19-23 | 5 (8.5%) | 2 (3.0%) | 7 (5.6%) |
| Waterlow skin type subscale, n (%) | | | |
| Healthy | 0 | 0 | 0 |
| Tissue paper | 11 (18.6%) | 28 (42.4%) | 39 (31.2%) |
| Dry and/or itching | 3 (5.1%) | 5 (7.6%) | 8 (6.4%) |
| Oedematous | 21 (35.6%) | 0 | 21 (16.8%) |
| Clammy, pyrexia | 0 | 0 | 0 |
| Discoloured, Stage 1 | 11 (18.6%) | 30 (45.5%) | 41 (32.8%) |
| Pressure ulcer/injury, Stage 2, 3 or 4+ | 13 (22%) | 3 (4.5%) | 16 (12.8%) |

Example 7: Spatial SEM Readings (Arm I Versus Arm II)

Data comparing spatial SEM readings at and around the heel indicated a higher mean 'center' SEM reading of 1.87 (SD=0.839) for Arm I subjects compared to 1.68 (SD=0.465) for Arm II subjects. The mean difference 0.20 (95% confidence interval (CI): −0.05-0.44) did not reach statistical significance (p=0.118). Mean readings outside of the erythema (ring 3) for the medial point were higher (mean SEM=2.1, SD=0.677) in Arm I subjects compared to similarly located points on those in Arm II unaffected by PI/PUs (mean 1.83, SD=0.506) with a mean difference of 0.27 (95% CI: 0.05-0.49, p=0.018). Mean SEM reading difference for the lateral point between Arm I and Arm II subjects was 0.13 (95% CI: −0.06-0.32), p=0.086), approaching statistical significance.

In sacral locations, the mean center SEM reading (2.18, SD=1.013) was lower in Arm I subjects (p=0.184) compared to Arm II (mean=2.36, SD=0.375). The SEM readings at the periphery of the erythema (ring 2) and outside of the erythema (ring 3) were higher in Arm I (PI/PU) subjects compared to similarly located points on those unaffected by PI/PUs, with the differences for the left and right points of ring 2 and all the points of ring 3 reaching statistical significance (p<0.05).

Example 8: SEM Readings within Arm I and Arm II

In Arm I subjects, the mean SEM readings for each subsequent ring increased as the ring increased in distance from the center of the heel PI/PU (1.92, SD=0.89). The mean SEM reading at the center of the heel PI/PU was statistically significantly lower than the readings collected at rings 2, 3, and 4 (p<0.01 in all cases) (Table 5).

TABLE 5

SUB-EPIDERMAL MOISTURE (SEM) READINGS BY RING
FOR PRESSURE INJURY/ULCER (PI/PU) ON HEEL

| Estimates | Centre | SEM scanner placement | | | |
|---|---|---|---|---|---|
| | | Ring 1 | Ring 2 | Ring 3 | Ring 4 |
| Mean (SE) | 1.92 (0.10) | 2.03 (0.09) | 2.14 (0.09) | 2.20 (0.09) | 2.25 (0.09) |
| 95% CI | (1.72, 2.13) | (1.87, 2.21) | (1.97, 2.32) | (2.03, 2.37) | (2.09, 2.44) |
| Comparisons to center | | | | | |
| Difference (SE) | | 0.12 (0.07) | 0.22 (0.07) | 0.28 (0.07) | 0.34 (0.07) |
| 95% CI | | (−0.03, 0.26) | (0.07, 0.37) | (0.13, 0.42) | (0.19, 0.49) |
| Two-sided p-value | | 0.121 | 0.003 | <0.001 | <0.001 |

CI—confidence interval;
SE—standard error

Similarly, the mean SEM reading at the center of the wounds was 2.18 (SD=1.01) and mean readings increased as the ring increased in distance from the center of the PI/PU (p<0.001 in all cases) (Table 6).

TABLE 6

SUB-EPIDERMAL MOISTURE (SEM) READINGS BY RING
FOR PRESSURE INJURY/ULCER (PI/PU) ON SACRUM

| Estimates | Centre | SEM Scanner Placement | | | |
|---|---|---|---|---|---|
| | | Ring 1 | Ring 2 | Ring 3 | Ring 4 |
| Mean (SE) | 2.18 (0.09) | 2.36 (0.06) | 2.58 (0.06) | 2.79 (0.06) | 2.85 (0.06) |
| 95% CI | (2.01, 2.35) | (2.23, 2.47) | (2.47, 2.71) | (2.67, 2.90) | (2.73, 2.97) |
| Comparisons to center | | | | | |
| Difference (SE) | | 0.17 (0.08) | 0.41 (0.08) | 0.61 (0.08) | 0.67 (0.08) |
| 95% CI | | (0.02, 0.33) | (0.25, 0.57) | (0.45, 0.76) | (0.51, 0.82) |
| Two-sided p-value | | 0.029 | <0.001 | <0.001 | <0.001 |

CI—confidence interval;
SE—standard error

In Arm II subjects SEM readings at and around the bony prominence of the sacrum were not significantly different (Kruskal-Wallis chi-square=8.49, p=0.0753). However, readings at and around the bony prominence of the heel were significantly different (Kruskal-Wallis chi-square=12.49, p=0.0019).

Example 9: Confounder Evaluation

For Arm I subjects, SEM readings taken at the center of wounds did not show any significant associations between blanchable and non-blanchable erythema (p>0.10) or pain levels (p>0.45). SEM readings approached but did not reach statistical significance (Student's two sample t-test) by PI/PU stages (Stage I PI/PU versus deep tissue injury (DTI)) among subjects with heel PI/PUs (t=1.71, p=0.093) or among subjects with sacral PI/PUs (t=−1.93, p=0.059), meaning discriminating between types of intact skin PI/PUs using the SEM test was not definitive from this study.

For Arm II, all of the subject characteristics, medical history and visual evaluation variables were considered as potential confounders. Repeated measures analysis of variance (ANOVA) was used to evaluate the variation due to the potential confounder (between-subject variability, or 'model' variability) compared to the variation due to anatomical location (within-subject variability, or 'error' remaining). Results from ANOVA showed no association between gender and the spatial SEM readings (p=0.4435). However, the Mann-Whitney-Wilcoxon rank sum test indicated that the SEM readings taken above the bony prominence of the heel were lower in male subjects than female (F test of the null hypothesis of no between-subject variability due to gender, F=4.16, p=0.0468). No other associations between readings at the heel and gender were observed. Calluses on the heel were identified as a potential confounder for heel SEM readings (F test of the null hypothesis of no between-subject variability due to calluses, F=15.87, p=0.0002) as was race (F test of the null hypothesis of no between-subject variability due to race, F=9.83, p=0.003).

Example 10: Sensitivity and Specificity Algorithms for Clinical Interpretation of the SEM Delta Value To determine the optimal cut-off to use for clinical interpretation of the SEM delta, a range of cut-offs was considered using the two algorithms (Table 7). With Algorithm A applied to sacral SEM values, a sensitivity of 90.9% was seen at the delta≥0.6 cut-off and a specificity of 98% was seen at the delta≥0.9 cut-off. In contrast, SEM readings at the heel showed the highest sensitivity (92.1%) at delta≥0.5 and the highest sensitivity (96%) was seen at the delta≥0.7 cut-off. For Algorithm B, ≥0.6 and ≥0.7 indicated an 87.9% sensitivity for sacral SEM with an 88% specificity at ≥0.9. For heel locations, this model showed an 85.7% sensitivity at ≥0.5 and a specificity of 58% at ≥0.8. The SEM delta of ≥0.6 cut-off was chosen to prioritize sensitivity over specificity.

TABLE 7

CONFIDENCE INTERVALS ON SENSITIVITY AND SPECIFICITY RESULTS

| Cut-off | TP | TN | FP | FN | Sensitivity | 95% CI | Specificity | 95% CI |
|---|---|---|---|---|---|---|---|---|
| Algorithm A (sacrum) | | | | | | | | |
| 20.6 | 60 | 43 | 7 | 6 | 90.9 | 84.0, −97.8 | 86 | 76.4, −95.6 |
| 20.7 | 52 | 46 | 4 | 14 | 78.8 | 68.9, −88.7 | 92 | 84.5, −99.5 |
| 20.8 | 50 | 46 | 4 | 16 | 75.8 | 65.4, −86.1 | 92 | 84.5, −99.5 |
| 20.9 | 41 | 49 | 1 | 25 | 62.1 | 50.4, −73.8 | 98 | 94.1, −100.0 |
| Algorithm B (sacrum) | | | | | | | | |
| 20.6 | 58 | 35 | 15 | 8 | 87.9 | 80.0, −95.8 | 70 | 57.3, −82.7 |
| 20.7 | 58 | 36 | 14 | 8 | 87.9 | 80.0, −95.8 | 72 | 59.6, −84.5 |
| 20.8 | 56 | 41 | 9 | 10 | 84.8 | 76.2, −93.5 | 82 | 71.4, −92.7 |
| 20.9 | 52 | 44 | 6 | 14 | 78.8 | 68.9, −88.7 | 88 | 79.0, −97.0 |
| Algorithm A (heels) | | | | | | | | |
| 20.6 | 52 | 45 | 5 | 11 | 82.5 | 73.2, −91.9 | 90 | 81.7, −98.3 |
| 20.7 | 44 | 48 | 0 | 19 | 69.8 | 58.5, −81.2 | 96 | 90.6, −100.0 |
| 20.8 | 32 | 50 | 0 | 31 | 50.8 | 38.5, −63.1 | 100 | 100.0, −100.0 |
| 20.9 | 26 | 50 | 0 | 37 | 41.3 | 29.1, −53.4 | 100 | 100.0, −100.0 |
| Algorithm B (heels) | | | | | | | | |
| 20.6 | 48 | 16 | 34 | 15 | 76.2 | 65.7, −86.7 | 32 | 19.1, −44.9 |
| 20.7 | 45 | 20 | 30 | 18 | 71.4 | 60.3, −82.6 | 40 | 26.4, −53.6 |
| 20.8 | 39 | 29 | 21 | 24 | 61.9 | 49.9, −73.9 | 58 | 44.3, −71.7 |
| >0.9 | 36 | 32 | 18 | 27 | 57.1 | 44.9 −69.4 | 64 | 50.7 −77.3 |

CI-confidence interval; FN-false negative; FP-false positive; TN-true negative; TP-true positive At sacral locations, Algorithm A resulted in a sensitivity of 90.9% (95% CI: 84.0-97.8) and specificity of 86% (95% CI: 76.4-95.6) for an SEM delta≥0.6 cut-off. Algorithm B resulted in 87.9% sensitivity (95% CI: 80.0-95.8) and 70% specificity (95% CI: 57.3-82.7) at the delta≥0.6 cut-off.

For the heels, Algorithm A resulted in 82.5% sensitivity (95% CI: 73.2-91.9) and 90% specificity (95% CI: 81.7-98.3) at the delta≥0.6 cut-off. Algorithm B for heels at delta≥0.6 resulted in a sensitivity of 76.2% (95% CI: 65.7-86.7) and a specificity of 32% (95% CI: 19.1-44.9). Aggregate (sacrum and heel) sensitivity and specificity analysis at delta≥0.6 using Algorithm A resulted in a sensitivity of 86.8% (n=112/129) and specificity of 88% (n=88/100). Sensitivity of 82.2% (n=106/129) and specificity of 51% (n=51/100) were noted using Algorithm B with delta≥0.6 (Table 8). ROC curve analysis conducted post hoc computed an area under the curve (AUC) of 0.9181 (95% CI: 0.8817, 0.9545, p<0.001) for Algorithm A and an AUC of 0.7809 (95% CI: 0.7221, 0.8397, p<0.0001) for Algorithm B.

A variety of further modifications and improvements in and to the compositions and methods of the present disclosure will be apparent to those skilled in the art based. The following non-limiting embodiments are envisioned:

Embodiment 1. A method for assessing tissue health at and around a target region, comprising the steps of:

obtaining a first plurality of SEM measurements at a first plurality of locations within a first tissue assessment area, obtaining a second plurality of SEM measurements at a second plurality of locations within a second tissue assessment area, calculating a first average of the first plurality of SEM measurements, calculating a second average of the second plurality of SEM measurements, calculating a difference between the second average and the first average, flagging that the tissue is damaged if the difference is greater than or equal to a cut-off threshold.

Embodiment 2. The method of embodiment 1, wherein the cut-off threshold is a predetermined number.

TABLE 8

AGGREGATE SENSITIVITY AND SPECIFICITY RESULTS

| | Algorithm A | | | Algorithm B | |
|---|---|---|---|---|---|
| | Arm I | Arm II | | Arm I | Arm II |
| Test positive | True positives 112 86.80% | False positives 12 12.00% | Test positive | True positives 106 82.20% | False positives 49 49.00% |
| Test negative | False negatives 17 13.20% | True negatives 88 88.00% | Test negative | False negatives 23 17.80% | True negatives 51 51.00% |
| | n* = 129 | n** = 100 | | n* = 129 | n** = 100 |

*n = 129 wounds on 125 subjects-Arm I
**n = 100 control sites on 50 subjects-Arm II Embodiment 3. The method of embodiment 2, wherein the cut-off threshold is a number ranging from about 0.6 to about 0.9.

Embodiment 4. The method of embodiment 2, wherein the cut-off threshold is about 0.6.

Embodiment 5. The method of embodiment 2, wherein the cut-off threshold is about 0.7.

Embodiment 6. The method of embodiment 2, wherein the cut-off threshold is about 0.8.

Embodiment 7. The method of embodiment 2, wherein the cut-off threshold is about 0.9.

Embodiment 8. The method of embodiment 1, wherein the first tissue assessment area is a circle centered on the target region and having a first radial distance.

Embodiment 9. The method of embodiment 8, wherein the second tissue assessment area is an annulus centered on the target region and having a second inner radial distance and a third outer radial distance from the target region.

Embodiment 10. The method of embodiment 9, wherein the second inner radial distance is greater than or equal to the first radial distance.

Embodiment 11. The method of embodiment 9, wherein the third outer radial distance is greater than the second inner radial distance.

Embodiment 12. The method of embodiment 8, wherein the first plurality of locations comprises a location in the center of the circle.

Embodiment 13. The method of embodiment 8, wherein the first plurality of locations comprises spatially distinct points within the circle.

Embodiment 14. The method of embodiment 8, wherein the first plurality of locations comprises spatially distinct points along one or more concentric rings within the circle, and wherein the one or more concentric rings are centered on the target region.

Embodiment 15. The method of embodiment 8, wherein the first plurality of locations comprises spatially distinct points along two lines dividing the circle into four quadrants.

Embodiment 16. The method of embodiment 9, wherein the second plurality of locations comprises spatially distinct points within the annulus.

Embodiment 17. The method of embodiment 9, wherein the second plurality of locations comprises spatially distinct points along one or more concentric rings within the annulus, and wherein the one or more concentric rings are centered on the target region.

Embodiment 18. The method of embodiment 9, wherein the second plurality of locations comprises spatially distinct points along two lines dividing the annulus into four quadrants.

Embodiment 19. The method of embodiment 1, wherein the first plurality of SEM measurements consists of 1 to 9 measurements.

Embodiment 20. The method of embodiment 1, wherein the second plurality of SEM measurements consists of 3 to 8 measurements.

Embodiment 21. The method of embodiment 1, wherein the target region is a bony prominence selected from the group consisting of a sacrum, a heel, a sternum, a scapula, an elbow, a thoracic spine, a trochanter, an ischium, and an ear.

Embodiment 22. The method of embodiment 1, wherein the target region is a fleshy tissue.

Embodiment 23. The method of embodiment 1, wherein the target region is within an erythema.

Embodiment 24. The method of embodiment 1, wherein the target region is within a healthy tissue.

Embodiment 25. A system for assessing tissue health at and around a target region, comprising:
(a) a Sub-Epidermal Moisture (SEM) scanner configured to make SEM measurements;
(b) a processor electronically coupled to the SEM scanner and configured to receive the SEM measurements; and
(c) a non-transitory computer readable media that is electronically coupled to the processor and comprises instructions stored thereon that, when executed on the processor, performs the steps of:
(i) receiving a first plurality of SEM measurements at a first plurality of locations within a first tissue assessment area,
(ii) receiving a second plurality of SEM measurements at a second plurality of locations within a second tissue assessment area,
(iii) calculating a first average of the first plurality of SEM measurements,
(iv) calculating a second average of the second plurality of SEM measurements,
(v) calculating a difference between the second average and the first average,
(vi) indicating that the tissue is damaged if the difference is greater than or equal to a cut-off threshold.

Embodiment 26. The system of embodiment 25, wherein the cut-off threshold is a predetermined number.

Embodiment 27. The system of embodiment 26, wherein the cut-off threshold is a number ranging from about 0.6 to about 0.9.

Embodiment 28. The system of embodiment 26, wherein the cut-off threshold is about 0.6.

Embodiment 29. The system of embodiment 26, wherein the cut-off threshold is about 0.7.

Embodiment 30. The system of embodiment 26, wherein the cut-off threshold is about 0.8.

Embodiment 31. The system of embodiment 26, wherein the cut-off threshold is about 0.9.

Embodiment 32. The system of embodiment 25, wherein the first tissue assessment area is a circle centered on the target region and having a first radial distance.

Embodiment 33. The system of embodiment 32, wherein the second tissue assessment area is an annulus centered on the target region and having a second inner radial distance and a third outer radial distance from the target region.

Embodiment 34. The system of embodiment 33, wherein the second inner radial distance is greater than or equal to the first radial distance.

Embodiment 35. The system of embodiment 33, wherein the third outer radial distance is greater than the second inner radial distance.

Embodiment 36. The system of embodiment 32, wherein the first plurality of locations comprises a location in the center of the circle.

Embodiment 37. The system of embodiment 32, wherein the first plurality of locations comprises spatially distinct points within the circle.

Embodiment 38. The system of embodiment 32, wherein the first plurality of locations comprises spatially distinct points along one or more concentric rings within the circle, and wherein the one or more concentric rings are centered on the target region.

Embodiment 39. The system of embodiment 32, wherein the first plurality of locations comprises spatially distinct points along two lines dividing the circle into four quadrants.

Embodiment 40. The system of embodiment 33, wherein the second plurality of locations comprises spatially distinct points within the annulus.

Embodiment 41. The system of embodiment 33, wherein the second plurality of locations comprises spatially distinct points along one or more concentric rings within the annulus, and wherein the one or more concentric rings are centered on the target region.

Embodiment 42. The system of embodiment 33, wherein the second plurality of locations comprises spatially distinct points along two lines dividing the annulus into four quadrants.

Embodiment 43. The system of embodiment 25, wherein the first plurality of SEM measurements consists of 1 to 9 measurements.

Embodiment 44. The system of embodiment 25, wherein the second plurality of SEM measurements consists of 3 to 8 measurements.

Embodiment 45. The system of embodiment 25, wherein the target region is a bony prominence selected from the group consisting of a sacrum, a heel, a sternum, a scapula, an elbow, a thoracic spine, a trochanter, an ischium, and an ear.

Embodiment 46. The system of embodiment 25, wherein the target region is a fleshy tissue.

Embodiment 47. The system of embodiment 25, wherein the target region is within an erythema.

Embodiment 48. The system of embodiment 25, wherein the target region is within a healthy tissue.

The invention claimed is:

1. A system for assessing tissue health at and around a target region, comprising:
   (a) a Sub-Epidermal Moisture (SEM) scanner comprising one or more sensors configured to make SEM measurements;
   (b) a processor electronically coupled to the SEM scanner and configured to receive the SEM measurements; and
   (c) a non-transitory computer readable medium electronically coupled to the processor and comprising instructions stored thereon that, when executed on the processor, performs the steps of:
   (i) receiving in the processor a first plurality of SEM measurements at a first plurality of SEM measurement locations within a first tissue assessment area, wherein the first tissue assessment area is a circle centered on the target region and having a first radial distance,
   (ii) receiving in the processor a second plurality of SEM measurements at a second plurality of SEM measurement locations within a second tissue assessment area, wherein the second tissue assessment area is an annulus centered on the target region and having a second inner radial distance and a third outer radial distance from the target region, and wherein the second plurality of SEM measurement locations comprises at least two SEM measurement locations that have different radial distances from the target region,
   (iii) calculating a first average of the first plurality of SEM measurements,
   (iv) calculating a second average of the second plurality of SEM measurements,
   (v) calculating a difference between the second average and the first average,
   (vi) providing an indication that the tissue is damaged when the difference is greater than or equal to a cut-off threshold.

2. The system of claim 1, wherein the cut-off threshold is a predetermined number.

3. The system of claim 2, wherein the cut-off threshold is a number ranging from about 0.6 to about 0.9.

4. The system of claim 2, wherein the cut-off threshold is about 0.6.

5. The system of claim 2, wherein the cut-off threshold is about 0.7.

6. The system of claim 2, wherein the cut-off threshold is about 0.8.

7. The system of claim 2, wherein the cut-off threshold is about 0.9.

8. The system of claim 1, wherein the second inner radial distance is greater than or equal to the first radial distance.

9. The system of claim 1, wherein the third outer radial distance is greater than the second inner radial distance.

10. The system of claim 1, wherein the first plurality of SEM measurement locations comprises a location in the center of the circle.

11. The system of claim 1, wherein the first plurality of SEM measurement locations comprises spatially distinct points within the circle.

12. The system of claim 1, wherein the first plurality of SEM measurement locations comprises spatially distinct points along one or more concentric rings within the circle, and wherein the one or more concentric rings are centered on the target region.

13. The system of claim 1, wherein the first plurality of SEM measurement locations comprises spatially distinct points along two lines dividing the circle into four quadrants.

14. The system of claim 1, wherein the second plurality of SEM measurement locations comprises spatially distinct points within the annulus.

15. The system of claim 1, wherein the second plurality of SEM measurement locations comprises spatially distinct points along one or more concentric rings within the annulus, and wherein the one or more concentric rings are centered on the target region.

16. The system of claim 1, wherein the second plurality of SEM measurement locations comprises spatially distinct points along two lines dividing the annulus into four quadrants.

17. The system of claim 1, wherein the first plurality of SEM measurements consists of 1 to 9 measurements.

18. The system of claim 1, wherein the second plurality of SEM measurements consists of 3 to 8 measurements.

19. The system of claim 1, wherein the target region is a bony prominence selected from the group consisting of a sacrum, a heel, a sternum, a scapula, an elbow, a thoracic spine, a trochanter, an ischium, and an ear.

20. The system of claim 1, wherein the target region is a fleshy tissue.

21. The system of claim 1, wherein the target region is within an erythema.

22. The system of claim 1, wherein the target region is within a healthy tissue.

23. The system of claim 1, wherein the system provides an indication by displaying a message or an icon on a graphical user interface (GUI), or by producing a sound.

24. The system of claim 1, wherein the system displays a map of the first plurality and the second plurality of SEM measurement locations on a GUI.

* * * * *